(12) United States Patent
Iwama et al.

(10) Patent No.: US 11,300,580 B2
(45) Date of Patent: Apr. 12, 2022

(54) ANALYSIS DEVICE AND ANALYSIS METHOD

(71) Applicant: JVC KENWOOD CORPORATION, Yokohama (JP)

(72) Inventors: Shigehiko Iwama, Yokohama (JP); Makoto Itonaga, Yokohama (JP); Yuichi Hasegawa, Yokohama (JP); Koji Tsujita, Yokohama (JP); Masayuki Ono, Yokohama (JP); Makoto Igarashi, Yokohama (JP)

(73) Assignee: JVC KENWOOD CORPORATION, Yokohama (JP)

( * ) Notice: Subject to any disclaimer, the term of this patent is extended or adjusted under 35 U.S.C. 154(b) by 1051 days.

(21) Appl. No.: 15/938,415

(22) Filed: Mar. 28, 2018

(65) Prior Publication Data

US 2018/0217175 A1    Aug. 2, 2018

Related U.S. Application Data

(63) Continuation of application No. PCT/JP2016/058707, filed on Mar. 18, 2016.

(30) Foreign Application Priority Data

Sep. 30, 2015    (JP) .............. JP2015-193868

(51) Int. Cl.
*G01N 33/558* (2006.01)
*G01N 35/04* (2006.01)
*G01N 37/00* (2006.01)
(Continued)

(52) U.S. Cl.
CPC .......... *G01N 35/04* (2013.01); *G01D 5/3473* (2013.01); *G01N 21/01* (2013.01); *G01N 21/62* (2013.01);
(Continued)

(58) Field of Classification Search
CPC ............. G01N 35/04; G01N 33/54366; G01N 21/01; G01N 33/54346; G01N 35/00069;
(Continued)

(56) References Cited

U.S. PATENT DOCUMENTS

2003/0133840 A1*  7/2003  Coombs ........... G01N 33/54386
                                                                422/82.05

FOREIGN PATENT DOCUMENTS

EP          1486786 A1    12/2004
JP       2002-521666 A     7/2002
(Continued)

OTHER PUBLICATIONS

Extended European Search Report dated Jun. 6, 2018 in corresponding European Patent Application No. 16850704.4.
(Continued)

*Primary Examiner* — Christopher L Chin
(74) *Attorney, Agent, or Firm* — Nath, Goldberg & Meyer; Jerald L. Meyer

(57) ABSTRACT

An analysis device includes a turntable holding a substrate, an optical pickup driven in a direction perpendicular to a rotation axis of the turntable and configured to emit laser light to reaction regions and to receive reflected light from the respective reaction regions, an optical pickup drive circuit, and a controller. The reaction regions are formed at positions different from the center of the substrate. The center of the substrate is located on the rotation axis of the turntable. The optical pickup detects a reception level of the reflected light to generate a light reception level signal. The controller controls a turntable drive circuit to rotate the substrate, controls the optical pickup drive circuit to drive the optical pickup, and specifies the respective reaction regions in accordance with a positional information signal and the light reception level signal.

7 Claims, 28 Drawing Sheets

(51) Int. Cl.
  *G01N 33/543*  (2006.01)
  *G01N 21/01*  (2006.01)
  *G01N 35/00*  (2006.01)
  *G01N 21/62*  (2006.01)
  *G01D 5/347*  (2006.01)
  *G01N 21/55*  (2014.01)

(52) U.S. Cl.
  CPC ..... *G01N 33/543* (2013.01); *G01N 33/54346* (2013.01); *G01N 33/54366* (2013.01); *G01N 33/54373* (2013.01); *G01N 35/00069* (2013.01); *G01N 37/00* (2013.01); *B01L 2300/0803* (2013.01); *B01L 2300/0806* (2013.01); *G01N 2021/558* (2013.01); *G01N 2035/0444* (2013.01)

(58) Field of Classification Search
  CPC ...... G01N 21/62; G01N 37/00; G01N 33/543; G01N 33/54373; G01N 2021/558; G01N 2035/0444; G01D 5/3473; B01L 2300/0803; B01L 2300/0806

USPC ..... 356/244; 422/400, 402, 403, 404, 82.05, 422/64; 435/288.7; 436/164, 809
  See application file for complete search history.

(56) References Cited

FOREIGN PATENT DOCUMENTS

| | | |
|---|---|---|
| JP | 2006-322819 A | 11/2006 |
| JP | 2009-63310 A | 3/2009 |
| JP | 2015-127692 A | 7/2015 |
| WO | 2014/168020 A1 | 10/2014 |

OTHER PUBLICATIONS

PCT/ISA/237 dated May 31, 2016 issued in corresponding International Application No. PCT/JP2016/058707.

* cited by examiner

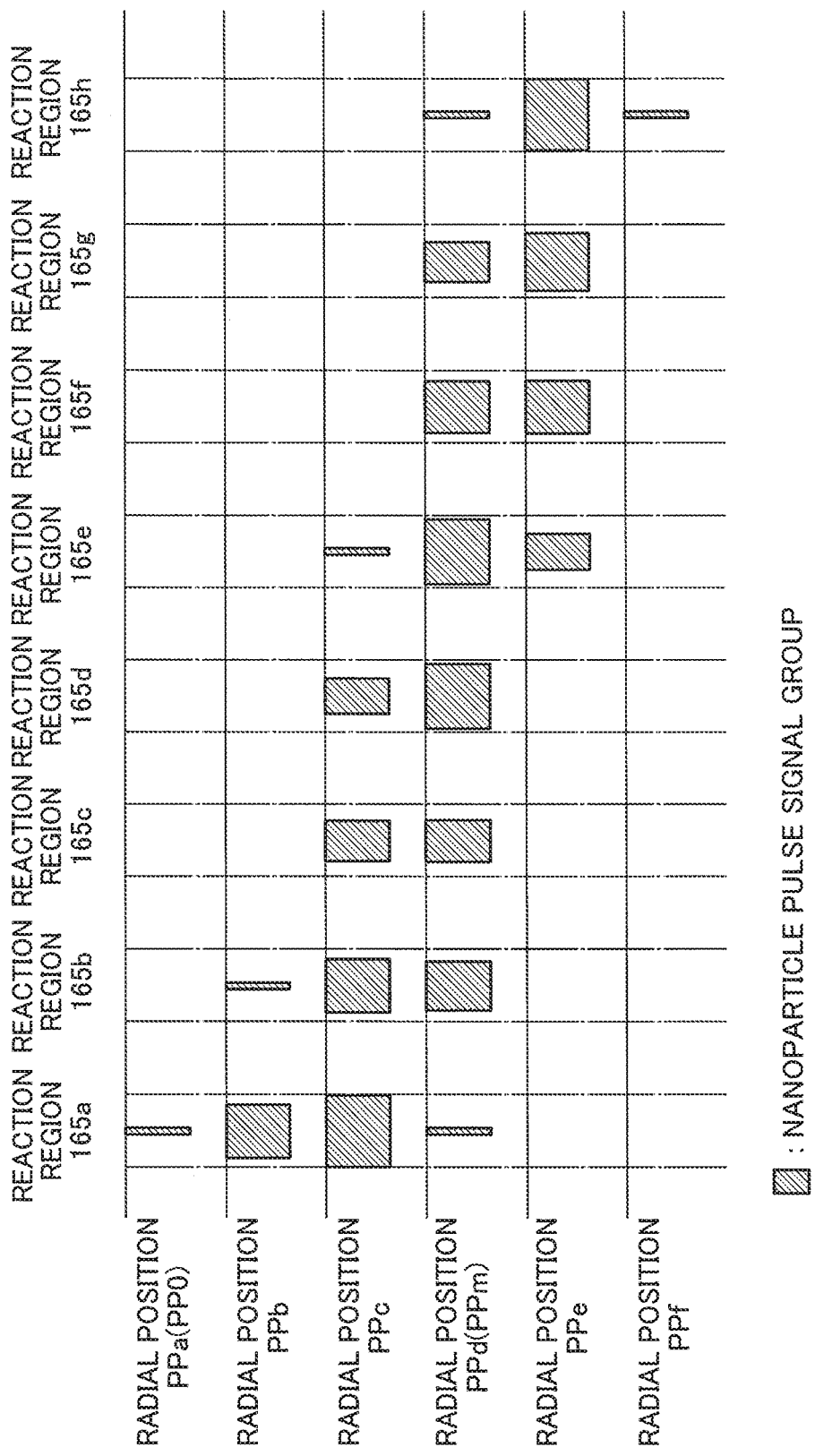

ANALYSIS DEVICE AND ANALYSIS METHOD

CROSS REFERENCE TO RELATED APPLICATION

This application is a Continuation of PCT Application No. PCT/JP2016/058707, filed on Mar. 18, 2016, and claims the priority of Japanese Patent Application No. 2015-193868, filed on Sep. 30, 2015, the entire contents of both of which are incorporated herein by reference.

BACKGROUND

The present disclosure relates to an analysis device and an analysis method for analyzing biomaterials such as antigens and antibodies.

Immunoassays are known to quantitatively analyze disease detection and therapeutic effects by detecting particular antigens or antibodies as biomarkers associated with diseases.

Japanese Translation of PCT International Application Publication No. 2002-521666 (hereinafter, referred to as Patent Document 1) and Japanese Unexamined Patent Application Publication No. 2006-322819 (hereinafter, referred to as Patent Document 2) disclose an analysis device in which antibodies that are fixed to a reaction region on a substrate of an optical disc are allowed to bind to antigens in a specimen, and the antigens are labeled by nanoparticles having antibodies and then are scanned with laser light emitted from an optical pickup so as to detect the nanoparticles captured on the reaction region on the substrate.

The analysis device disclosed in Patent Documents 1 and 2 is an optical disc device utilized for detecting a specimen.

SUMMARY

The conventional analysis device as disclosed in Patent Documents 1 and 2 moves the optical pickup in a radial direction of the substrate being rotated. The substrate is provided with a plurality of reaction regions. Therefore, a reaction region in which nanoparticles are detected needs to be specified.

The analysis device disclosed in Patent Document 1 specifies a reaction region by use of address information of the optical disc. In the analysis device disclosed in Patent Document 2, the substrate includes a group of pits in which positional information of reaction regions is recorded.

The conventional analysis device as disclosed in Patent Documents 1 and 2 thus needs to preliminarily record the positional information of the reaction regions on the substrate of the optical disc. Accordingly, the process of manufacturing the substrate is complicated to increase manufacturing costs for the substrate.

A first aspect of one or more embodiments provides an analysis device including: a turntable holding a substrate having a plurality of reaction regions for capturing nanoparticles to be analyzed; a turntable drive unit configured to rotate the turntable; a turntable drive circuit configured to control the turntable drive unit; an optical pickup driven in a direction perpendicular to a rotation axis of the turntable, and configured to emit laser light to the respective reaction regions and receive reflected light from the respective reaction regions; an optical pickup drive circuit configured to control an operation of the optical pickup; and a controller configured to control the turntable drive circuit and the optical pickup drive circuit, wherein the plurality of reaction regions are formed at positions different from a center of the substrate, the substrate is held by the turntable such that the center is located on the rotation axis of the turntable, the optical pickup drive circuit detects a position of the turntable in the direction perpendicular to the rotation axis of the turntable to generate a positional information signal, the optical pickup detects a reception level of the reflected light from the respective reaction regions to generate a light reception level signal, and the controller controls the turntable drive circuit to rotate the substrate, controls the optical pickup drive circuit to move the optical pickup in the direction perpendicular to the rotation axis of the turntable, and specifies the respective reaction regions in accordance with the positional information signal and the light reception level signal.

A second aspect of one or more embodiments provides an analysis method including: rotating a substrate of which a center is a rotation axis, the substrate having a plurality of reaction regions formed at positions different from the center of the substrate to capture nanoparticles to be analyzed; emitting laser light to the respective reaction regions from a predetermined position in a direction perpendicular to the rotation axis of the substrate and receiving reflected light from the respective reaction regions; and specifying the respective reaction regions in accordance with positional information on the predetermined position and a reception level of the reflected light.

BRIEF DESCRIPTION OF THE DRAWINGS

FIG. 26 is a schematic view for describing a relationship between the respective radial positions and time widths of nanoparticle pulse signal groups in the respective reaction regions.

DETAILED DESCRIPTION

First Embodiment

An analysis device and an analysis method according to a first embodiment are described below with reference to FIG. 1A to FIG. 18.

[Reaction Regions of Substrate]

Reaction regions of a substrate are described with reference to FIG. 1A to FIG. 5.

Figure 1A:
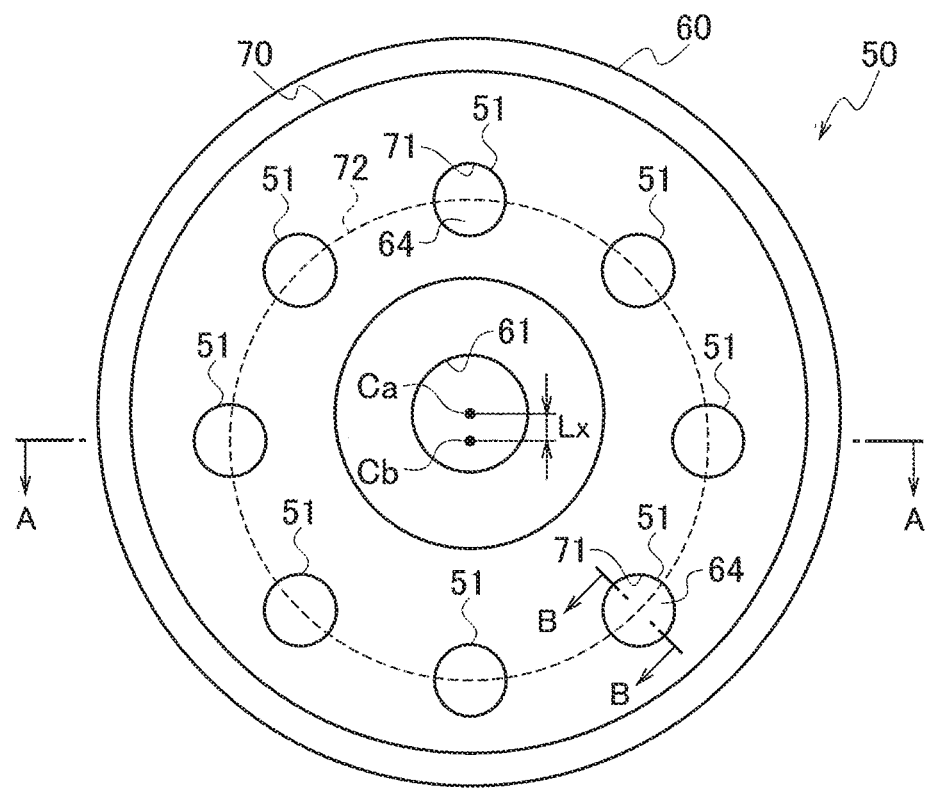
FIG. 1A is a schematic top view of an antigen capture unit according to a first embodiment.
Figure 1B:
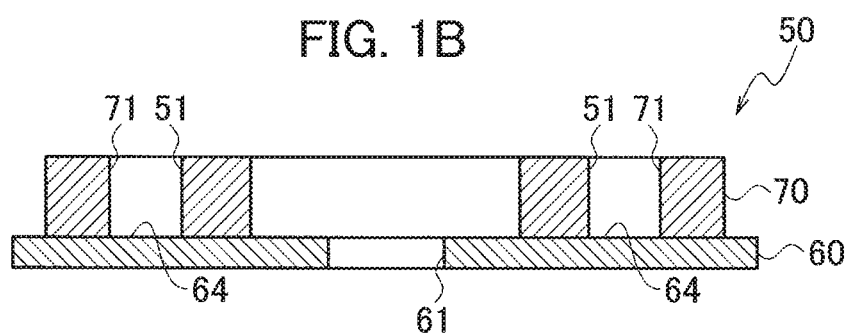
FIG. 1B is a schematic cross-sectional view taken along line A-A in FIG. 1A.
Figure 1C:
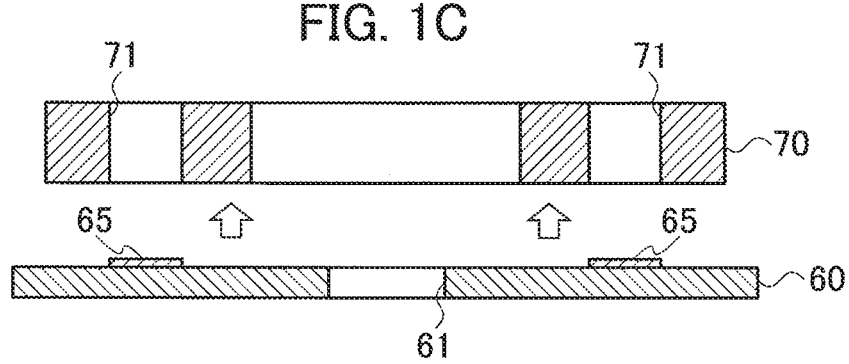
FIG. 1C is a schematic cross-sectional view illustrating a cartridge which is detachable from a substrate.

FIG. 1A is a schematic top view of an antigen capture unit 50 for forming reaction regions 65 on a substrate 60 (shown in FIG. 1C). FIG. 1B is a schematic cross-sectional view taken along line A-A in FIG. 1A. FIG. 1C is a schematic cross-sectional view illustrating a cartridge 70 which is detachable from the substrate 60. FIG. 1C corresponds to FIG. 1B.

As shown in FIG. 1A and FIG. 1B, the antigen capture unit 50 includes the substrate 60 and the cartridge 70.

The substrate 60 is formed into a circular shape having substantially the same dimensions of optical discs such as Blu-ray discs (BDs), digital versatile discs (DVDs), and compact discs (CDs). The substrate 60 is provided with a positioning hole 61 in the middle.

The substrate 60 is formed of resin material such as polycarbonate resin or cycloolefin polymer, commonly used for optical discs. The substrate is not limited to the optical discs described above and may be any optical disc according to other embodiments or conforming to prescribed standards.

Figure 2:
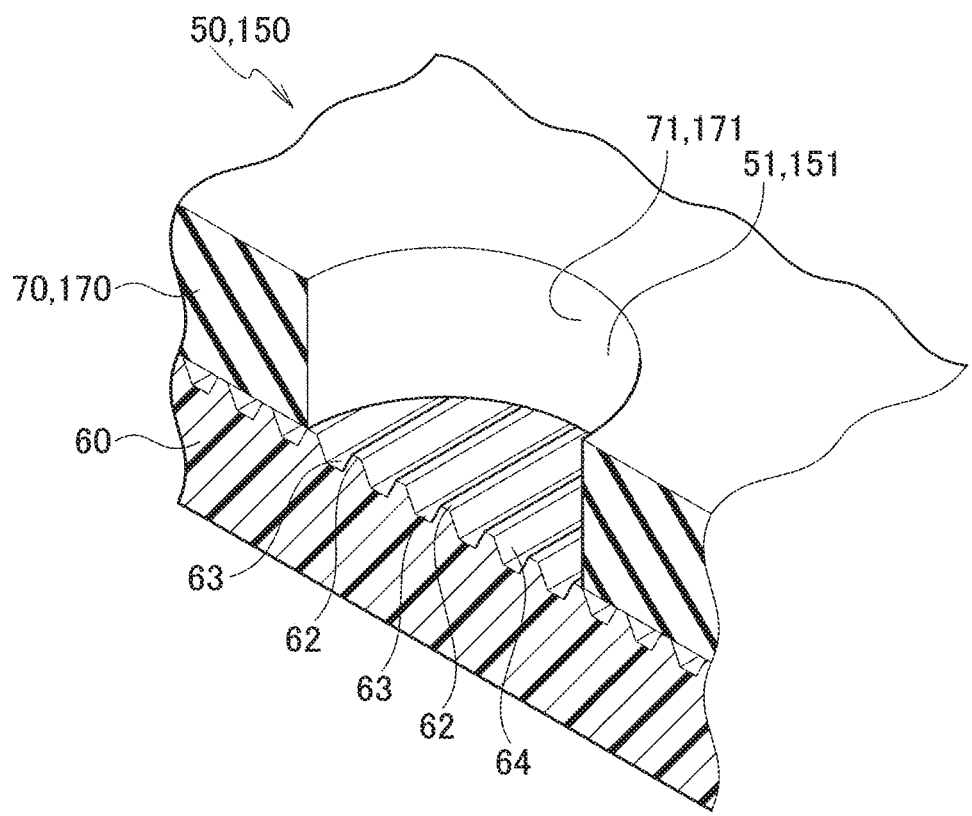
FIG. 2 is a partly enlarged perspective view showing a well cross-sectioned along line B-B in FIG. 1A and line D-D in FIG. 19A.
Figure 3:
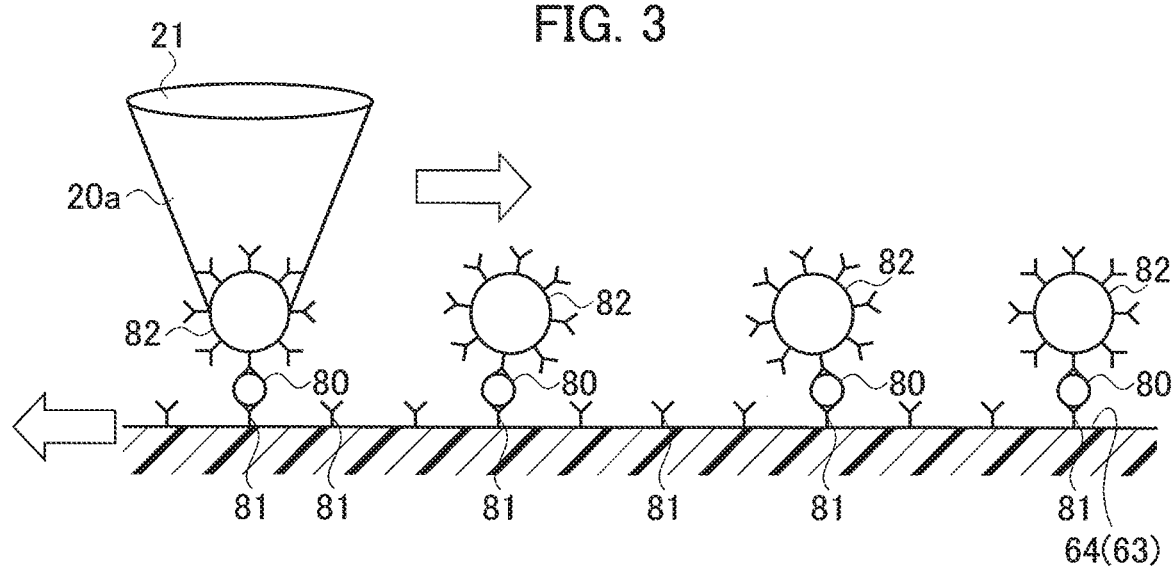
FIG. 3 is an enlarged cross-sectional view schematically illustrating a state in which antigens are captured and sandwiched between nanoparticles and antibodies in a recess of a track region.
Figure 4:
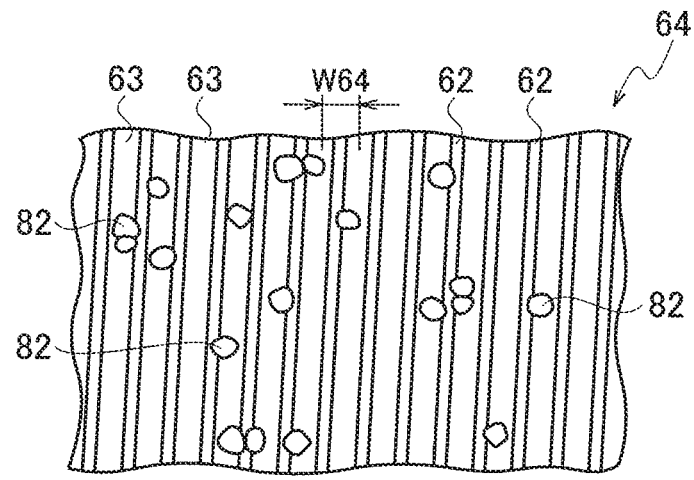
FIG. 4 is an enlarged plan view schematically illustrating a state in which nanoparticles are captured in the recesses of the track region.

FIG. 2 is a partly enlarged perspective view cross-sectioned along line B-B in FIG. 1A. FIG. 3 is an enlarged cross-sectional view schematically showing a state in which antigens 80 are captured and sandwiched between nanoparticles 82 and antibodies 81 on a recess 63 in a track region 64. FIG. 4 is an enlarged schematic view showing a state in which the nanoparticles 83 are captured on the recesses 63 in the track region 64.

As shown in FIG. 2, the surface of the substrate 60 includes the track regions 64 provided with convex regions 62 and the recesses 63 alternately arranged in a radial direction. The convex regions 62 and the recesses 63 are formed in a spiral from the inner side to the outer side of the substrate 60. The convex regions 62 correspond to lands of an optical disc. The recesses 63 correspond to grooves of an optical disc. A track pitch W64 of the recesses 63 (the convex regions 62) in the radial direction shown in FIG. 4 is 320 nm, for example.

As shown in FIG. 1A, the cartridge 70 has a ring-like shape. The cartridge 70 is provided with a plurality of cylindrical penetration holes 71 arranged along the circumferential direction.

The penetration holes 71 are arranged at regular intervals such that the respective center points are located on a circumference 72 of the common circle of which the center Cb is separated by a predetermined distance Lx from the center Ca of the substrate 60.

As shown in FIG. 1B and FIG. 2, the antigen capture unit 50 includes a plurality of wells 51 defined by the penetration holes 71 of the cartridge 70 and the track regions 64 of the substrate 60. The inner surface of the penetration holes 71 corresponds to the inner surface of the wells 51, and the track regions 64 of the substrate 60 corresponds to the bottoms of the wells 51. The wells 51 each serve as a holder for storing a solution such as a sample solution or a buffer solution.

Although FIG. 1A illustrates the antigen capture unit 50 including eight wells 51, the number of wells 51 is not limited to eight.

As shown in FIG. 3, when a buffer solution including the antibodies 81 which specifically bind to the antigens 80, which is specific protein, is injected into the wells 51, the antibodies 81 are fixed to the track regions 64 as solid-phase antibodies. Hereinafter, the antibodies 81 are referred to as solid-phase antibodies 81.

When a sample solution including the antigens 80 is injected into the wells 51, the antigens 80 are specifically bound to the solid-phase antibodies 81 and captured on the track regions 64, more particularly, captured on the recesses 63.

When a buffers solution including nanoparticles 82 to which antibodies specifically binding to the antigens 80 are fixed is injected into the wells 51, the nanoparticles 82 to be analyzed specifically bind to the antigens 80 captured on the recesses 63 in the track regions 64 so as to be captured on the recesses 63 as labeling antibodies. Accordingly, the antigens 80 are captured and sandwiched between the solid-phase antibodies 81 and the nanoparticles 82 as labeling antibodies on the recesses 63 in the track regions 64.

FIG. 4 illustrates the state in which the antigens 80 are captured and sandwiched between the solid-phase antibodies 81 and the nanoparticles 82 on the recesses 63 in the track regions 64. The spherical particles are the nanoparticles 82. The nanoparticles 82 are captured on the recesses 63.

As shown in FIG. 1C, the cartridge 70 is detachable from the substrate 60. The nanoparticles 82 are detected only by use of the substrate 60 detached from the cartridge 70.

Figure 5:
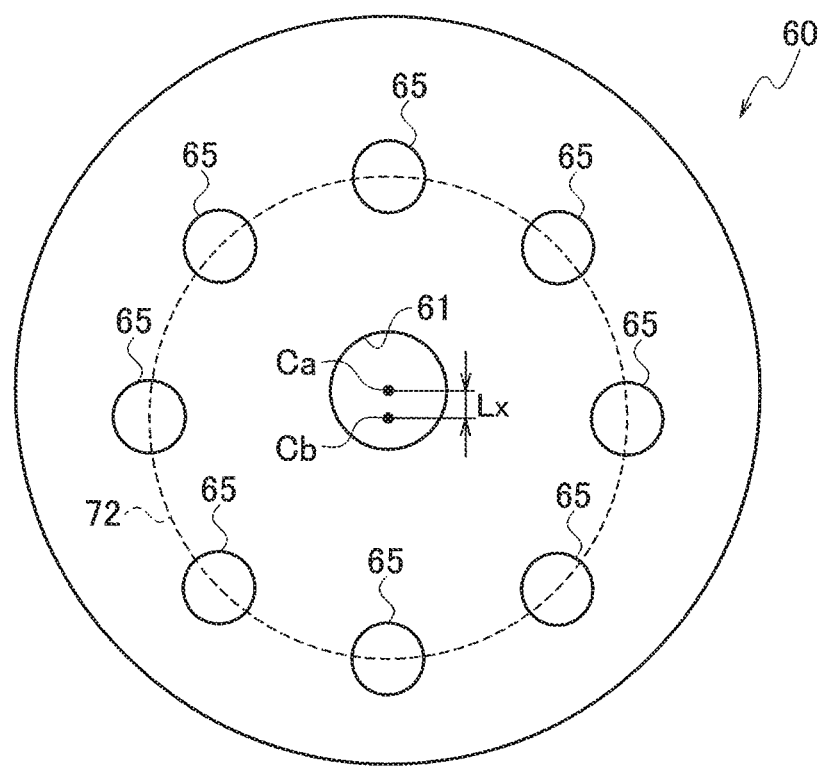
FIG. 5 is a schematic top view of a substrate including reaction regions formed by use of the antigen capture unit according to a first embodiment.

FIG. 5 is a schematic view of the substrate 60 including the reaction regions 65 formed by use of the antigen capture unit 50.

The track regions 64 corresponding to the bottoms of the wells 51 on the substrate 60 serve as the respective reaction regions 65 on which the antigens 80 and the nanoparticles 82 are captured by an antigen-antibody reaction. The substrate 60 is thus provided with the plurality of reaction regions 65 for capturing the nanoparticles 82 to be analyzed, corresponding to the respective wells 51.

The plurality of reaction regions 65 are arranged at regular intervals such that the respective center points are located on the circumference 72 of the common circle of which the center Cb is separated by the predetermined distance Lx from the center Ca of the substrate 60, as in the case of the wells 51.

Although FIG. 5 illustrates the substrate 60 including eight reaction regions 65 corresponding to the eight wells 51, the number of reaction regions 65 is not limited to eight, as in the case of the wells 51.

[Analysis Device]

Figure 6:
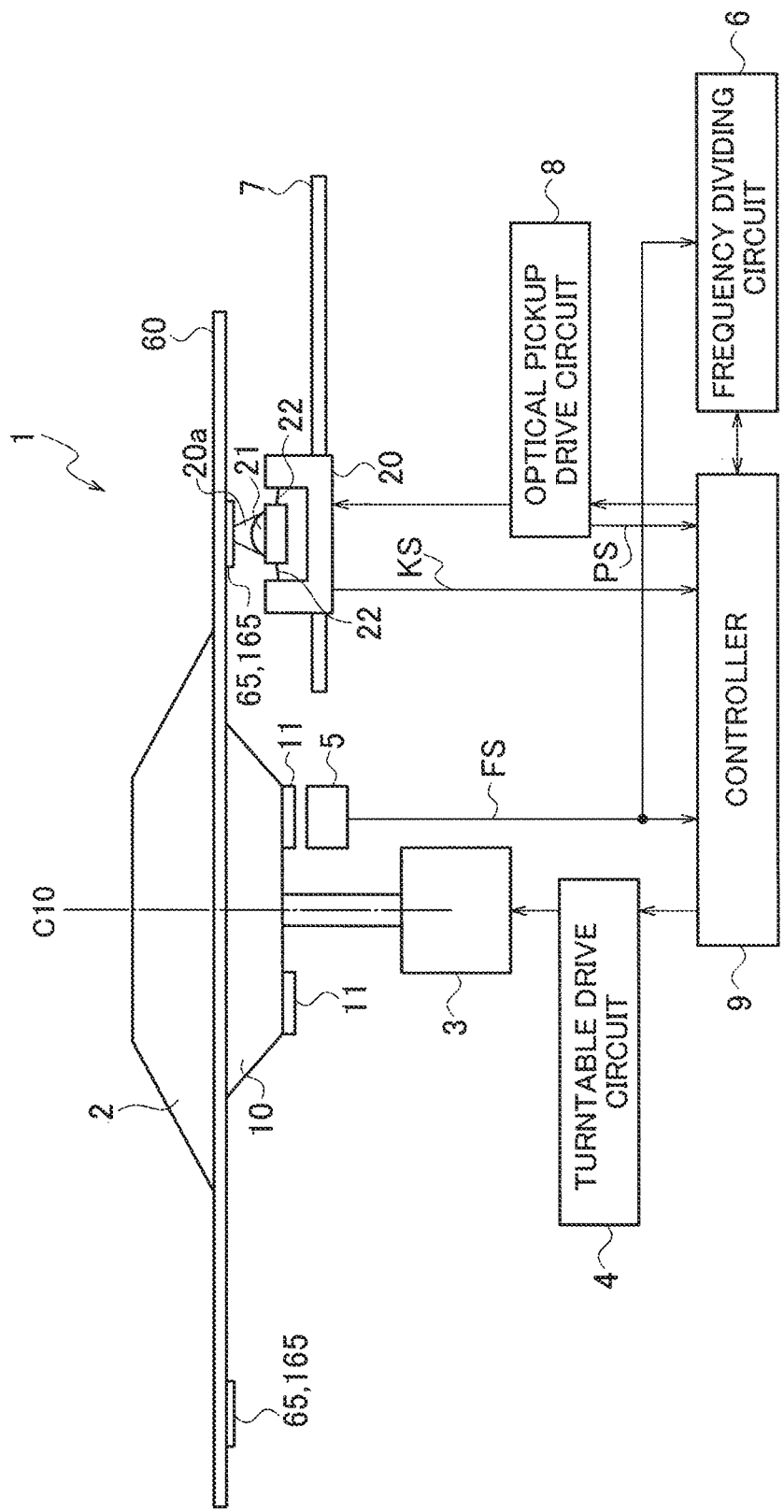
FIG. 6 is a configuration diagram showing an analysis device according to a first embodiment.
Figure 7:
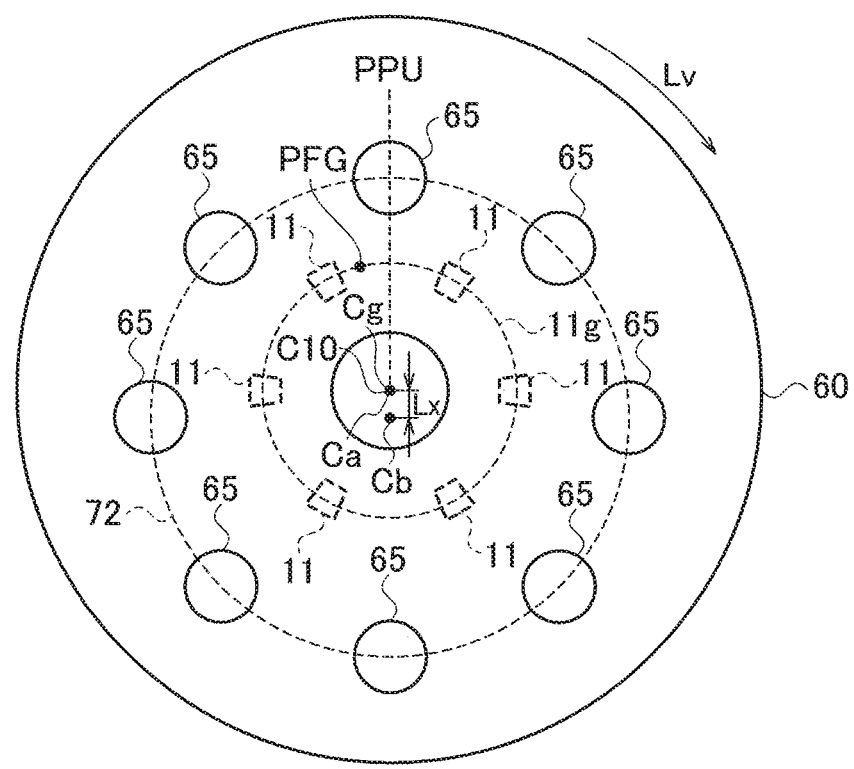
FIG. 7 is a schematic top view for describing a positional relationship between the respective reaction regions and a detecting position of an optical pickup and a positional relationship between FG elements and a detecting position of a turntable rotation detecting sensor according to a first embodiment.

FIG. 6 is a configuration diagram showing an analysis device 1 according to a first embodiment. FIG. 7 is a schematic top view for describing a positional relationship between the respective reaction regions 65 and a detecting position PPU of the optical pickup 20 and a positional relationship between frequency generator (FG) elements 11 and a detecting position PFG of a turntable rotation detecting sensor 5.

As shown in FIG. 6, the analysis device 1 includes a turntable 10, a clamper 2, a turntable drive unit 3, a turntable drive circuit 4, a turntable rotation detecting sensor 5, a frequency dividing circuit 6, a guide shaft 7, the optical pickup 20, an optical pickup drive circuit 8, and a controller 9.

The substrate 60 is placed on the turntable 10 with the reaction regions 65 facing down.

The turntable 10 includes a plurality of FG elements 11 fixed to the surface 60 on the opposite side of the surface on which the substrate 60 is placed (on the lower side in FIG. 6).

As shown in FIG. 7, the plurality of FG elements 11 are arranged at regular intervals on a circumference 11g of a circle of which the center Cg is located on a rotation axis C10 of the turntable 10.

Although FIG. 7 illustrates the turntable 10 including six FG elements 11, the number of FG elements 11 is not limited to six.

The clamper 2 is driven in directions separating from and approaching the turntable 10, namely, in the upper and lower directions in FIG. 6. The substrate 60 is held on the turntable 10 between the clamper 2 and the turntable 10 when the clamper 2 is driven in the lower direction.

In particular, the substrate 60 is held such that the center Ca is located on the rotation axis C10 of the turntable 10. The substrate 60 is also held such that the reaction regions 65 are arranged at regular intervals and the respective center points are located on the circumference 72 of the common circle of which the center Cb is separated by the predetermined distance Lx from the rotation axis C10 of the turntable 10.

The turntable drive unit 3 rotates the turntable 10 on the rotation axis C10 together with the substrate 60 and the clamper 2. A spindle motor may be used as the turntable drive unit 3.

The turntable drive circuit 4 controls the turntable drive unit 3. For example, the turntable drive circuit 4 controls the turntable drive unit 3 to rotate the turntable 10 at a constant linear velocity Lv together with the substrate 60 and the clamper 2.

The turntable rotation detecting sensor 5 is arranged close to the turntable 10 so as to be opposed to the FG elements 11.

As shown in FIG. 7, the turntable rotation detecting sensor 5 (refer to FIG. 6) is located at the detecting position PFG on the circumference 11g on which the FG elements 11 are arranged at regular intervals. The turntable rotation detecting sensor 5 is a magnetic sensor for detecting a magnetic field generated by the FG elements 11. The FG elements 11 are thus detected at the detecting position PFG.

When the turntable 10 is rotated, the FG elements 11 pass through a point adjacent to the turntable rotation detecting sensor 5. The turntable rotation detecting sensor 5 detects the magnetic field of the FG elements 11 passing through the point adjacent to the turntable rotation detecting sensor 5 and generates an FG pulse signal FS, so as to output the signal to the frequency dividing circuit 6 and the controller 9.

The FG pulse signal FS is output at a frequency proportional to a velocity of rotation (a linear velocity) of the turntable 10. Namely, the FG pulse signal FS is a turntable rotation detecting signal for detecting the rotation of the turntable 10.

The frequency dividing circuit 6 subjects the input FG pulse signal FS to frequency dividing processing. A frequency dividing ratio is set to the same number of the FG elements 11 arranged on the turntable 10. For example, when the six FG elements 11 are arranged on the turntable 10, the frequency dividing ratio is set to six. The frequency dividing processing may be implemented by a piece of software in the controller 9 without the frequency dividing circuit 6 provided.

The guide shaft 7 is placed in parallel to the substrate 60 in the radial direction of the substrate 60. The guide shaft 7 is arranged in a direction perpendicular to the rotation axis C10 of the turntable 10.

The optical pickup 20 is supported by the guide shaft 7. The optical pickup 20 is driven along the guide shaft 7, in the radial direction of the substrate 60, and parallel to the substrate 60. The optical pickup 20 is thus driven in a direction perpendicular to the rotation axis C10 of the turntable 10.

The optical pickup 20 includes an objective lens 21. The objective lens 21 is supported by suspension wires 22. The objective lens 21 is driven in the directions separating from and approaching the substrate 60, namely, in the upper and lower directions in FIG. 6.

The optical pickup 20 emits laser light 20a to the substrate 60. The laser light 20a is condensed by the objective lens 21 on the surface provided with the reaction regions 65 of the substrate 60 (on the lower surface of the substrate 60 in FIG. 6).

The optical pickup 20 receives the reflected light from the substrate 60. The optical pickup 20 detects a reception level of the reflected light, generates a light reception level signal KS, and outputs the signal to the controller 9.

The detecting position PPU shown in FIG. 7 corresponds to an axial line of the guide shaft 7. The optical pickup 20 is moved from the inner side to the outer side of the substrate 60 along the axial line of the guide shaft 7. The respective reaction regions 65 are thus detected at the detecting position PPU by the optical pickup 20.

The optical pickup drive circuit 8 controls the operation of the optical pickup 20. The optical pickup drive circuit 8 moves the optical pickup 20 along the guide shaft 7 or moves the objective lens 21 of the optical pickup 20 in the vertical direction, for example.

The optical pickup drive circuit 8 detects a position in the substrate 60 in the radial direction, generates a positional information signal PS, and outputs the signal to the controller 9.

The controller 9 controls the turntable drive circuit 4, the frequency dividing circuit 6, and the optical pickup drive circuit 8. A central processing unit (CPU) may be used as the controller 9, for example.

The controller 9 controls the rotation of the turntable 10, namely, the rotation of the substrate 60 via the turntable drive circuit 4 according to the FG pulse signal FS output from the turntable rotation detecting sensor 5.

The controller 9 controls the operation of the optical pickup 20 according to the positional information signal PS output from the optical pickup drive circuit 8.

The controller 9 analyzes the light reception level signal KS output from the optical pickup 20 so as to detect the nanoparticles 82 to be analyzed.

[Analysis Method]

Figure 8A:
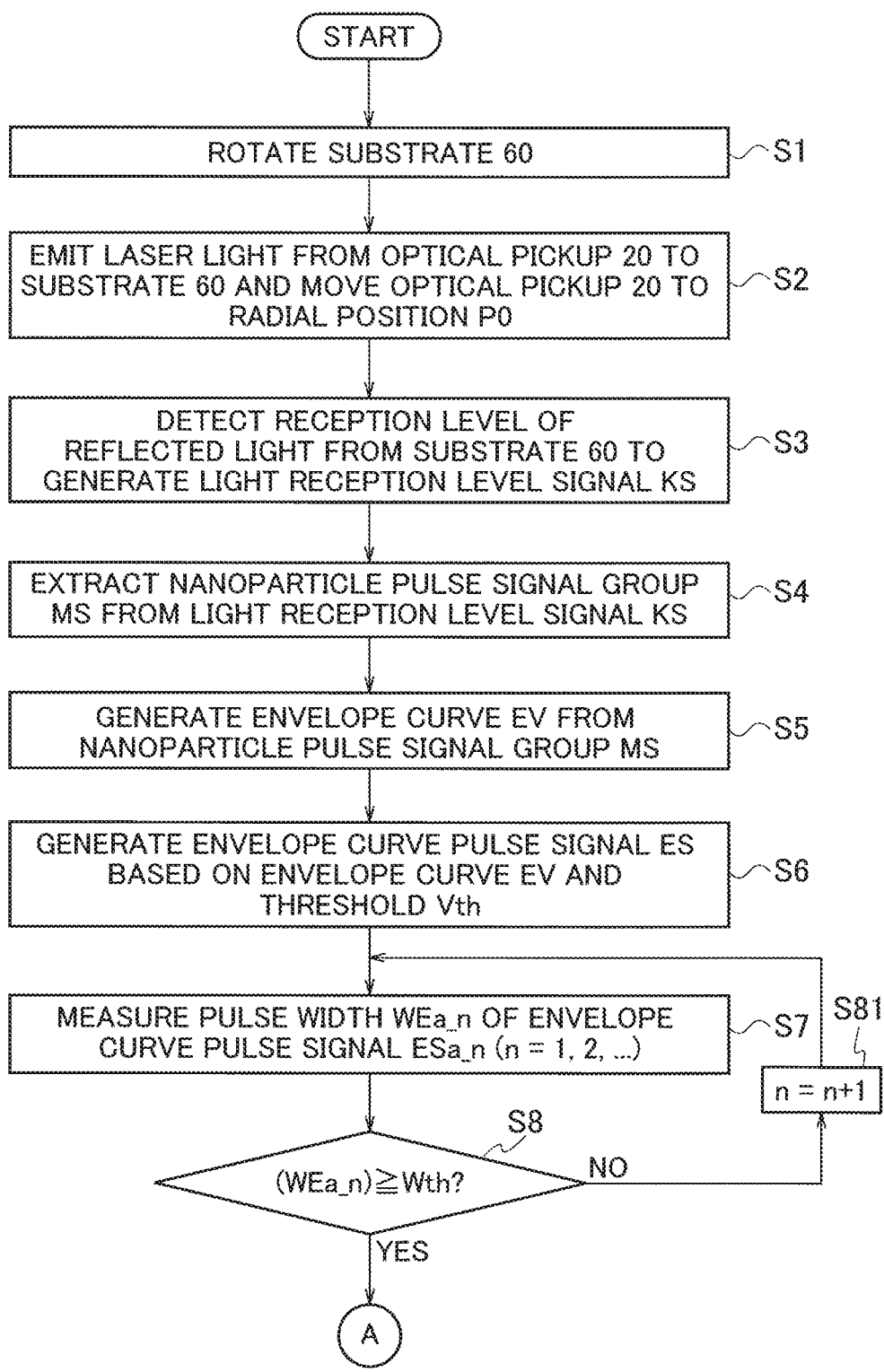
FIG. 8A is a flow chart for describing an analysis method according to a first embodiment.
Figure 8B:
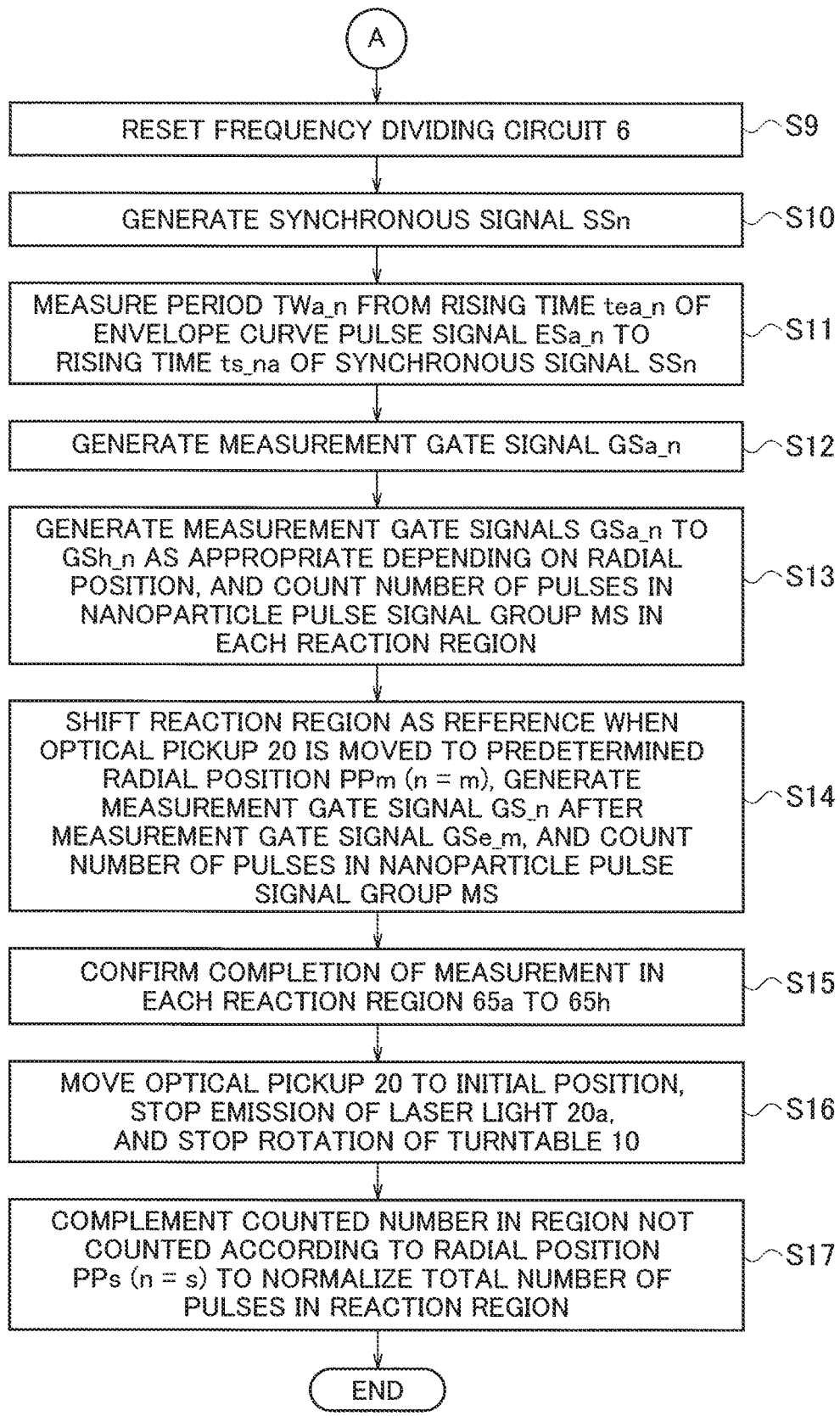
FIG. 8B is a flow chart for describing the analysis method according to a first embodiment.
Figure 9:
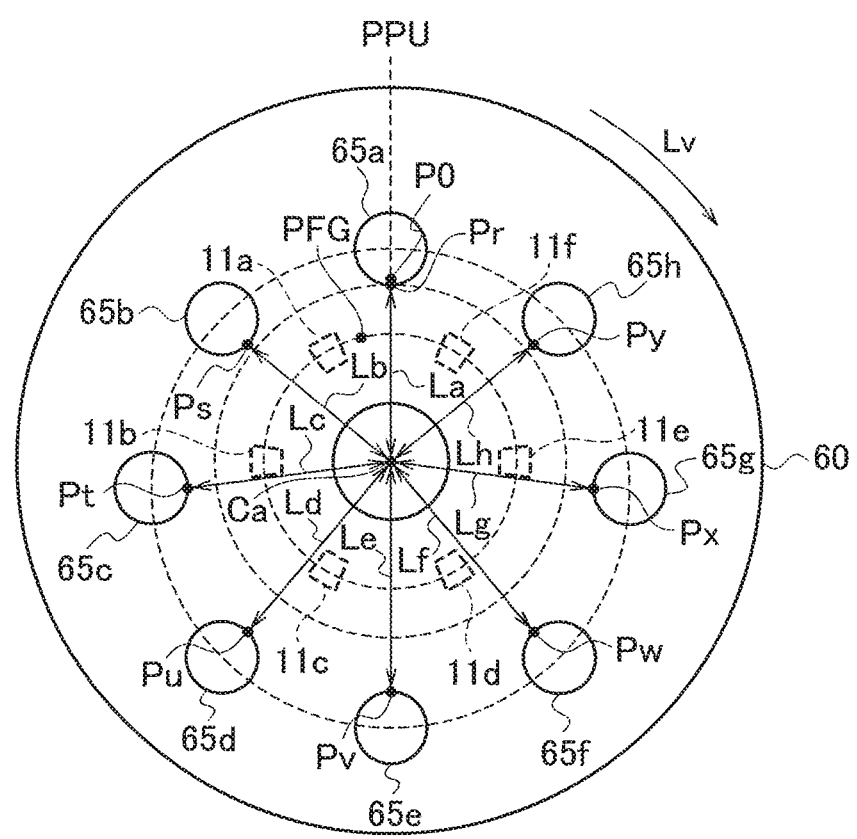
FIG. 9 is a schematic top view for describing a positional relationship between the respective reaction regions and a radial position corresponding to the detecting position of the optical pickup.

FIG. 8A and FIG. 8B are flow charts for describing a method of analyzing the nanoparticles 82 by the analysis device 1. FIG. 9 is a schematic top view for describing a positional relationship between the respective reaction regions 65a to 65h and a radial position Pn corresponding to the reception-level detecting position of the optical pickup 20.

The respective reaction regions 65 (refer to FIG. 7) are sequentially indicated by the first reaction region 65a, the second reaction region 65b, the third reaction region 65c, the fourth reaction region 65d, the fifth reaction region 65e, the sixth reaction region 65f, the seventh reaction region 65g, and the eighth reaction region 65h in FIG. 9 for illustration purposes.

The distance from the center Ca of the substrate 60 to the radial position Pr (n=r) of the first reaction region 65a at the edge toward the center Ca is defined as La. The distance from the center Ca of the substrate 60 to the radial position Ps (n=s) of the second reaction region 65b is defined as Lb. The distance from the center Ca of the substrate 60 to the radial position Pt (n=t) of the third reaction region 65c is defined as Lc. The distance from the center Ca of the substrate 60 to the radial position Pu (n=u) of the fourth reaction region 65d is defined as Ld. The distance from the center Ca of the substrate 60 to the radial position Pv (n=v) of the fifth reaction region 65e is defined as Le. The distance from the center Ca of the substrate 60 to the radial position Pw (n=w) of the sixth reaction region 65f is defined as Lf. The distance from the center Ca of the substrate 60 to the radial position Px (n=x) of the seventh reaction region 65g is defined as Lg. The distance from the center Ca of the substrate 60 to the radial position Py (n=y) of the eighth reaction region 65h is defined as Lh.

The radial position Pn corresponds to the detecting position of the optical pickup 20 for detecting the respective reaction regions 65a to 65h. In particular, the radial position Pn is the reception-level detecting position on the detecting position PPU of the optical pickup 20 at which the optical pickup 20 emits the laser light 20a to the substrate 60 and receives the reflected light from the substrate 60. The radial position Pn is also a relative position based on the rotation axis C10 of the turntable 10 in the direction perpendicular to the rotation axis C10. The small letter "n" corresponds to the track number in the respective track regions 64.

The controller 9 can detect the radial position Pn according to the positional information signal PS output from the optical pickup drive circuit 8.

The respective distances La to Lh to the respective reaction regions 65a to 65h can be represented by the following relational expressions: La<Lb, Lb<Lc, Lc<Ld, Ld<Le, Lb=Lh, Lc=Lg, and Ld=Lf.

The respective FG elements 11 (refer to FIG. 7) are sequentially indicated by the first FG element 11a, the second FG element 11b, the third FG element 11c, the fourth FG element 11d, the fifth FG element 11e, and the sixth FG element 11f in FIG. 9 for illustration purposes.

In step S1 in FIG. 8A, the controller 9 controls the turntable drive circuit 4 to direct the turntable drive unit 3 to drive the turntable 2 so that the substrate 60 rotates at a constant linear velocity Lv.

In step S2, the controller 9 directs the optical pickup 20 to emit the laser light 20a to the substrate 60, and controls the optical pickup drive circuit 8 to move the optical pickup 20 to the radial position P0 (n=0) at which the distance from the center C1 of the substrate 60 is L0 (La=L0<Lb). The distance L0 is 24 mm, for example.

In step S3, the optical pickup 20 receives the reflected light from the substrate 60. The optical pickup 20 detects the reception level of the reflected light, generates a light reception level signal KS, and outputs the signal to the controller 9.

Figure 10A:
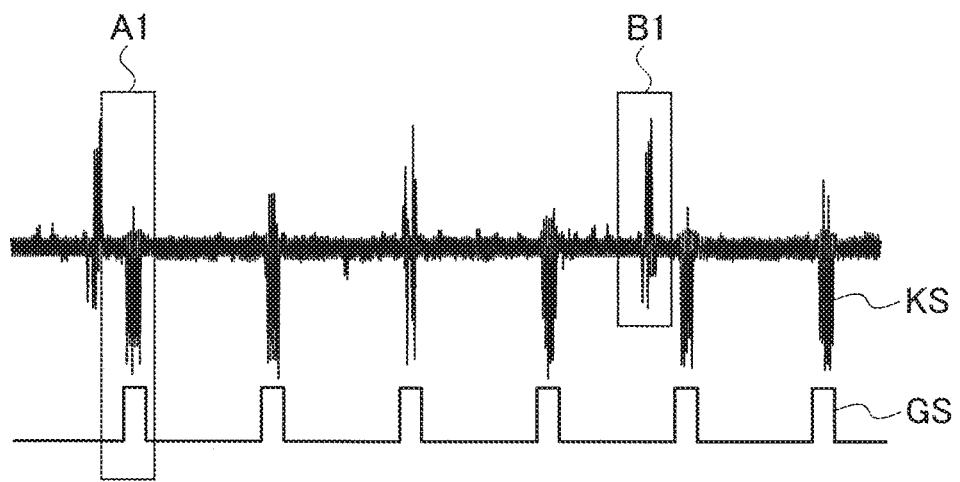
FIG. 10A is a view illustrating light reception level signals KS.
Figure 10B:
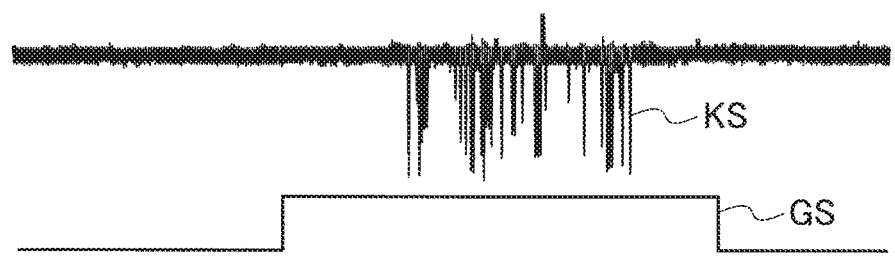
FIG. 10B is a partly enlarged view showing the region A1 in FIG. 10A.

FIG. 10A illustrates the light reception level signals KS. FIG. 10B is a partly enlarged view showing the region A1 in FIG. 10A. In FIG. 10A and FIG. 10B, the vertical axis represents a signal level, and the transverse axis represents a time. The signal level corresponds to the reception level detected by the optical pickup 20.

As shown in FIG. 3, when the optical pickup 20 is moved to the radial position P0 while the substrate 60 is being rotated, the laser light 20a scans the recess 63 at the radial position P0.

Since the amount of reflected light from the nanoparticles 82 is smaller than the amount of reflected light from the recess 63, the reception level detected by the optical pickup 20 decreases when the nanoparticles 62 are scanned with the laser light 20a.

Therefore, the region A1 shown in FIG. 10A indicates the light reception level signal KS in the reaction region 65 in which the nanoparticles 82 are captured.

Figure 11:
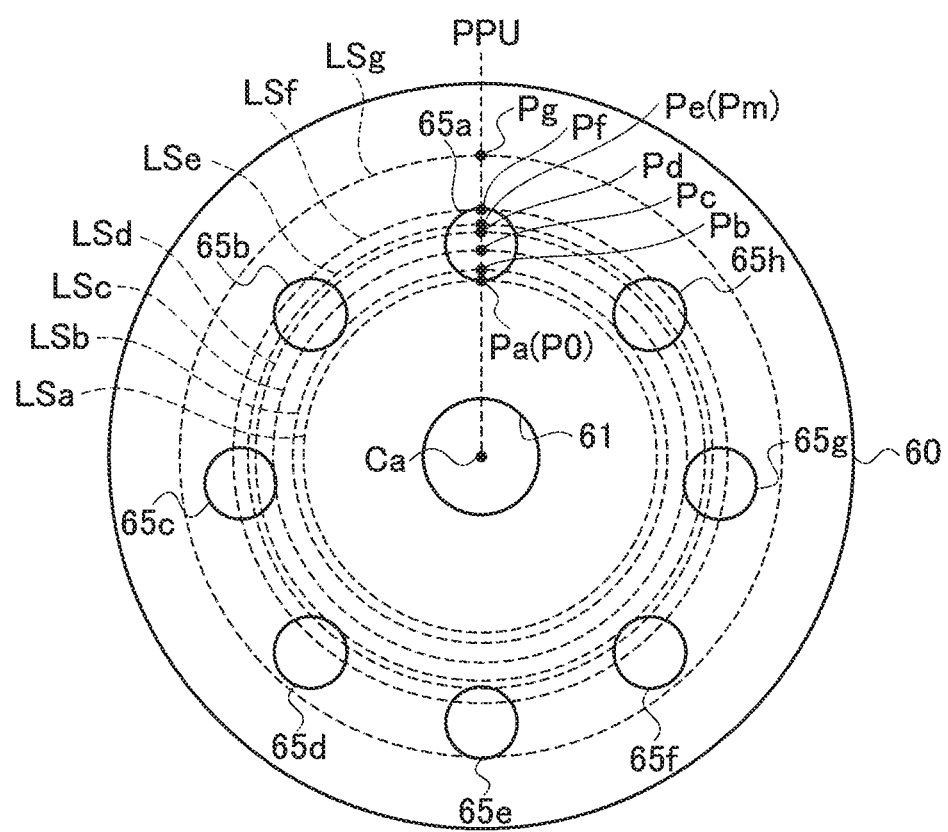
FIG. 11 is a schematic top view for describing a positional relationship between the respective reaction regions and the respective radial positions.

FIG. 11 is a schematic top view for describing a positional relationship between the respective reaction regions 65a to 65h and the respective radial positions Pa to Pg. The broken lines LSa to LSg in FIG. 11 schematically indicate loci obtained when the laser light 20a scans the respective radial positions Pa to Pg. The radial position Pa in FIG. 11 corresponds to the radial position P0.

When the optical pickup 20 is moved to the radial position P0 while the substrate 60 is being rotated, the laser light 20a scans the circumference of the circle passing through the radial position P00. Since the reaction region 65a is located closer to the center Ca than the other reaction regions 65b to 65h, only the reaction region 65a is scanned with the laser light 20a at the radial position P0.

The light reception level signal KS as shown in FIG. 10B is thus output from the optical pickup 20 to the controller 9 when the reaction region 65a is scanned with the laser light 20a at the radial position P0.

Figure 12:
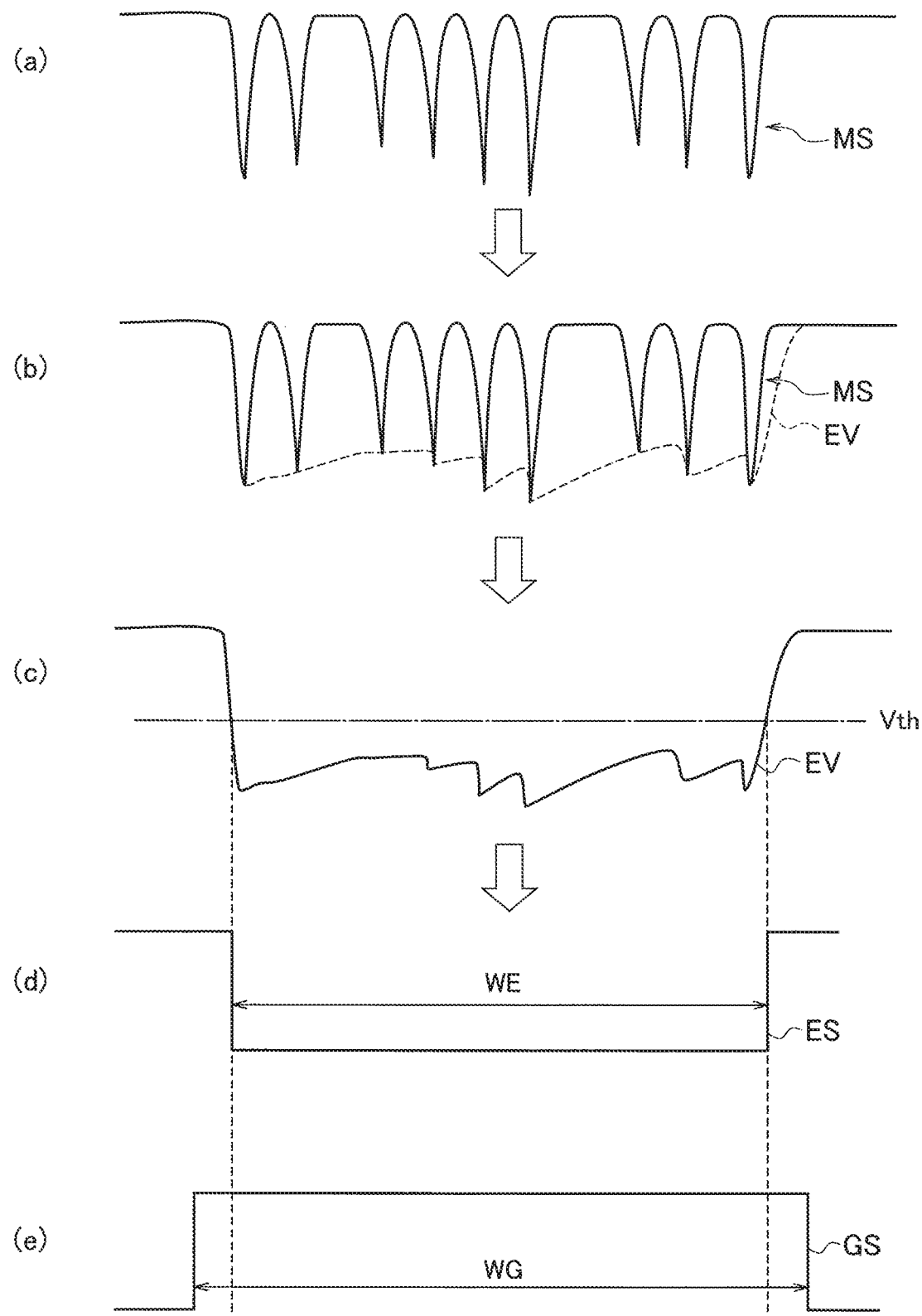
FIG. 12 is a schematic view for describing a relationship among a nanoparticle pulse signal group, an envelope curve, an envelope curve pulse signal, and a measurement gate signal.

(a) of FIG. 12 is a schematic view showing a nanoparticle pulse signal group. (b) of FIG. 12 is a schematic view showing an envelope curve. (c) of FIG. 12 is a schematic view showing a relationship between the envelope curve and a threshold. (d) of FIG. 12 is a schematic view showing an envelope curve pulse signal. (e) of FIG. 12 is a schematic view showing a measurement gate signal.

In step S4, the controller 9 subjects the light reception level signal KS to filter processing to extract the nanoparticle pulse signal group MS, as shown in (a) of FIG. 12.

In step S5, the controller 9 subjects the nanoparticle pulse signal group MS to envelope curve processing to generate the envelope curve EV, as shown in (b) of FIG. 12.

In step S6, the controller 9 generates the envelope curve pulse signal ES based on the envelope curve EV and a predetermined threshold Vth, as shown in (c) and (d) of FIG. 12.

In step S7, the controller 9 measures the pulse width WEa_n of the envelope curve pulse signal ESa_n in the reaction region 65a. The small letter "a" in the envelope curve pulse signal ESa_n and the pulse width WEa_n is the same adscript as in the reaction region 65a. The small letter "n" corresponds to the track number (n=0, 1, 2, . . . ).

In step S8, the controller 9 determines whether or not the pulse width WEa_n is greater than or equal to a predetermined pulse width Wth.

When the pulse width WEa_n is determined not to be greater than or equal to the predetermined pulse width Wth (NO), the controller 9 measures the pulse width WEa_n of the envelope curve pulse signal ESa_n in the reaction region 65a in the next track (n=n+1) after the substrate 60 makes one revolution in step 81.

When the pulse width WEa_n is determined to be greater than or equal to the predetermined pulse width Wth (YES), the controller 9 specifies the radial position Ps (n=s) at which the pulse width WEa_n is determined to be greater than or equal to the predetermined pulse width Wth. The controller 9 resets the frequency dividing circuit 6 in step S9 in FIG. 8B.

Figure 13:
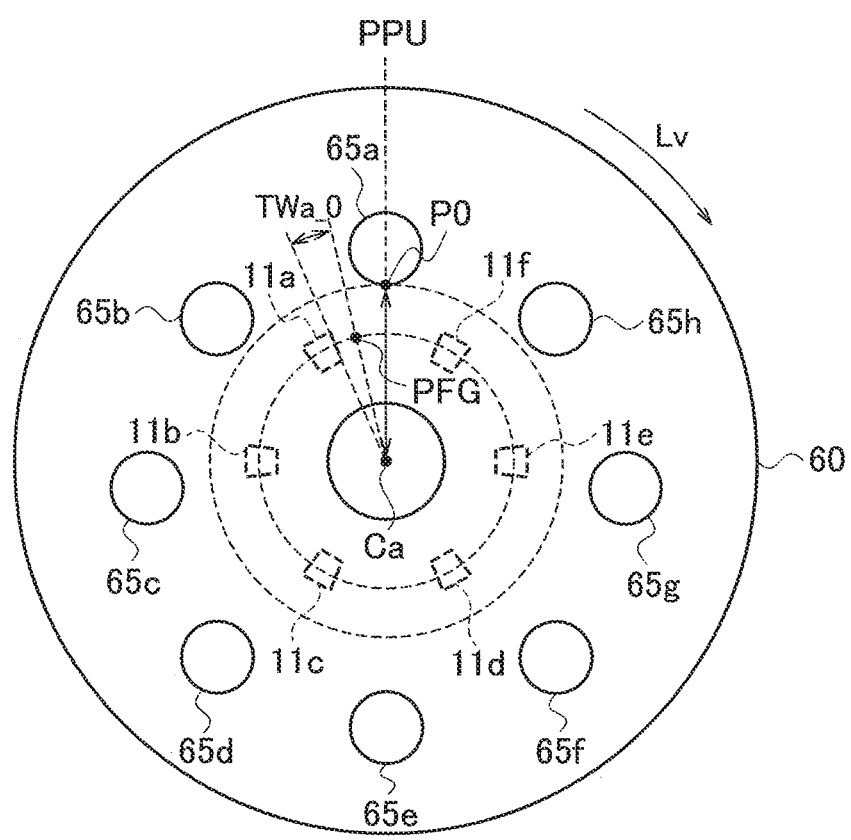
FIG. 13 is a schematic top view for describing a positional relationship between the respective reaction regions and the detecting position of the optical pickup when the optical pickup moves to a radial position P0 and a positional relationship between the respective FG elements and the detecting position of the turntable rotation detecting sensor.

FIG. 13 is a schematic top view for describing a positional relationship between the detecting position PPU of the optical pickup 20 and the respective reaction regions 65a to 65h when the optical pickup 20 is moved to the radial position P00, and a positional relationship between the respective FG elements 11a to 11h and the detecting position PFG of the turntable rotation detecting sensor 5.

FIG. 13 illustrates the state in which the optical pickup 20 is moved to the radial position P00, and the reaction region 65a is moved to the detecting position PPU.

Figure 14:
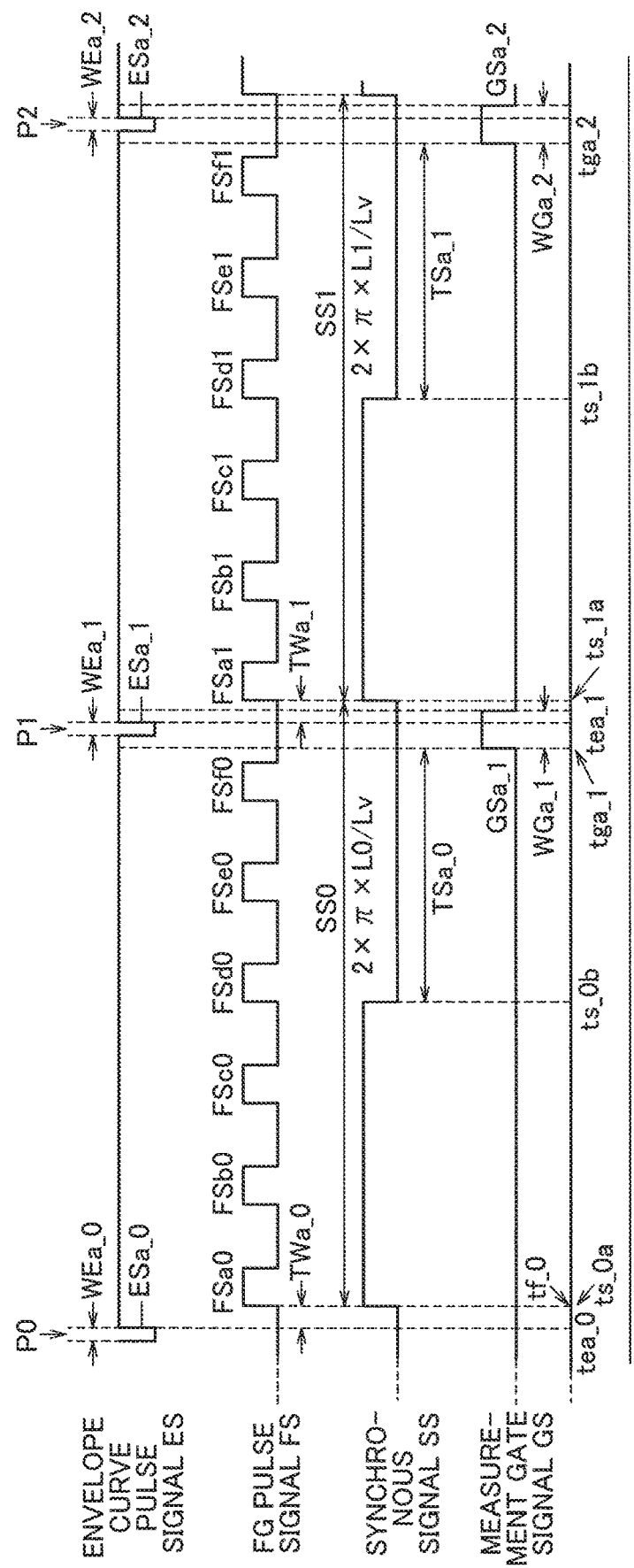
FIG. 14 is a time chart showing a relationship among the envelope curve pulse signal, an FG pulse signal, a synchronous signal, and the measurement gate signal.

FIG. 14 is a time chart showing the relationship among the envelope curve pulse signal ES, the FG pulse signal FS, a synchronous signal SS, and a measurement gate signal GS.

In the state shown in FIG. 13, when the pulse width WEa_0 (n=0) of the envelope curve pulse signal ESa_0 (n=0) shown in FIG. 14 is determined to be greater than or equal to the predetermined pulse width Wth (YES) in step S8, the controller 9 determines that the determined envelope curve pulse signal ESa_0 is the envelope curve pulse signal in the reaction region 65a in step S9.

Namely, the controller 9 specifies the reaction region 65a in accordance with the radial position P0 and the envelope curve pulse signal ESa_0. The other reaction regions 65b to 65h are specified in association with the positional relation to the reaction region 65a accordingly.

The controller 9 defines the central position of the envelope curve pulse signal ESa_0 as a measurement reference, and resets the frequency dividing circuit 6 at the rising time tea_0 (n=0) of the envelope curve pulse signal ESa_0.

The reason for the determination as to whether the pulse width WEa_0 of the envelope curve pulse signal ESa_0 is greater than or equal to the predetermined pulse width Wth is to exclude noise from a target to be detected, as indicated by the region B1 shown in FIG. 10A, for example.

Typically, a pulse width of an envelope curve pulse signal generated from noise is narrower than the pulse width of the envelope curve pulse signal generated from the nanoparticle pulse signal group MS. Therefore, the envelope curve pulse signal as a target to be detected can only be extracted such that the pulse width of the envelope curve pulse signal is determined so as to exclude noise from a target to be detected.

In step S10, the frequency dividing circuit 6 generates a synchronous signal SS0 rising synchronously with a rising point (time tf_0) of an FG pulse signal FSa0 (n=0) which is input first after the reset, as shown in FIG. 14. The frequency dividing circuit 6 keeps generating the synchronous signal SSn (n=1, 2, . . . ) after generating the synchronous signal SS0 during the rotation of the substrate 60.

The synchronous signal SSn is obtained such that the FG pulse signal FS is subjected to frequency division by the frequency dividing circuit 6. The period of the synchronous signal SSn conforms to the rotation period of the substrate 60. Namely, when the number of the FG elements 11 is six as shown in FIG. 13, the frequency dividing circuit 6 generates the synchronous signal SSn in which the FG pulse signal FS is divided into six frequencies.

In step S11, the controller 9 measures a time period TWa_0 (n=0) from the rising time tea_0 of the envelope curve pulse signal ESa_0 to the rising time ts_0a (n=0) of the synchronous signal SS0.

In step S12, the controller 9 generates a measurement gate signal GSa_1 (n=1) for counting the number of pulses of the nanoparticle pulse signal group MS in the reaction region 65a. The measurement gate signal GSa_n corresponds to the measurement gate signal GS shown in FIGS. 10A and 10B and (e) of FIG. 12.

As described above, the track pitch W64 is 320 nm, for example. The distance L0 from the center Ca of the substrate 60 to the radial position P0 is 24 mm, for example. The track pitch W64 is smaller by 0.0013% than the distance L0. The period of the synchronous signal SSn from the point at which the reaction region 65a is detected at the radial position P0 to the point at which the reaction region 65a is detected again after the substrate 60 makes one revolution, can be expressed by 2×π×L0/Lv (n=0). The reference sign Lv is a velocity of rotation (a linear velocity) of the substrate 60.

The rising point of the measurement gate signal GSa_1 for counting the number of pulses of the nanoparticle pulse signal group MS in the reaction region 65a at the radial position P1 after the substrate 60 makes one revolution from the radial position P00, is set to the time tga_1 after a lapse of a time period TSa_0 starting from a falling point (time ts_0b) of the synchronous signal SS0 and calculated according to the following Equation (1). In Equation (1), WGa_1 (n=1) is a pulse width of the measurement gate signal GSa_1 at the radial position P1. The pulse width WGa_n is preliminarily determined in association with the radial position Pn.

$$TSa\_0 = \frac{\pi \times L0}{Lv} - \left(\frac{WEa\_0}{2} + TWa\_0 + \frac{WGa\_1}{2}\right) \quad (1)$$

The rising point of the measurement gate signal GSa_2 at the radial position P2 after the substrate 60 makes one revolution from the radial position P1, is set to the time tga_2 after a lapse of a time period TSa_1 starting from a falling point (time ts_1b) of the synchronous signal SS1 (n=1). The time period TSa_1 is calculated in accordance with a pulse width WEa_1 (n=1), a time period TWa_1, and a pulse width WGa_2 (n=2) in the same manner as the time period calculated according to Equation (1).

The pulse width WEa_1 is a pulse width of the envelope curve pulse signal ESa_1 (n=1) in the reaction region 65a detected by the measurement gate signal GSa_1 at the radial position P1. The time period TWa_1 is a period from the rising time tea_1 of the envelope curve pulse signal ESa_1 to the rising time ts_1a of the synchronous signal SS1. The pulse width WGa_2 (n=2) is a pulse width of the measurement gate signal GSa_2 (n=2) at the radial position P2.

Therefore, the rising point of the measurement gate signal GSa_n is set to the time tga_n after a lapse of a time period TSa_n−1 starting from a falling point (time ts_n−1b) of the synchronous signal SSn−1 and calculated according to the following Equation (2).

$$TSa\_n-1 = \frac{\pi \times Ln-1}{Lv} - \left(\frac{WEa\_n-1}{2} + TWa\_n-1 + \frac{WGa\_n}{2}\right) \quad (2)$$

In Equation (2), Ln−1 is a distance from the center Ca of the substrate 60 to the radial position Pn−1, WEa_n−1 is a pulse width of the envelope curve pulse signal ESa_n−1 in the reaction region 65a detected by the measurement gate signal GSa_n−1 at the radial position Pn−1, TWa_n−1 is a period from the rising time tea_n−1 of the envelope curve pulse signal ESa_n−1 to the rising time ts_n−1a of the synchronous signal SSn−1, and WGa_n is a pulse width of the measurement gate signal GSa_n at the radial position Pn.

The controller 9 thus generates the measurement gate signal GSa_n synchronous with the envelope curve pulse signal ESa_n.

In step S13, the controller 9 counts the number of pulses of the nanoparticle pulse signal group MS in the reaction region 65a in accordance with the light reception level signal KS detected in a predetermined period (the pulse width WGa_n) regulated by the measurement gate signal GSa_n, and adds the counted number in each track (n=0, 1, 2, . . . ) together.

The total number of the nanoparticles 82 in the reaction region 65a thus can be measured such that the number of the pulses of the nanoparticle pulse signal group MS in the reaction region 65a is counted in each track (n=0, 1, 2, . . . ) and added together. The measurement of the number of the nanoparticles 82 can lead to the indirect measurement of the particular antigens 80 associated with a disease.

Figure 15:
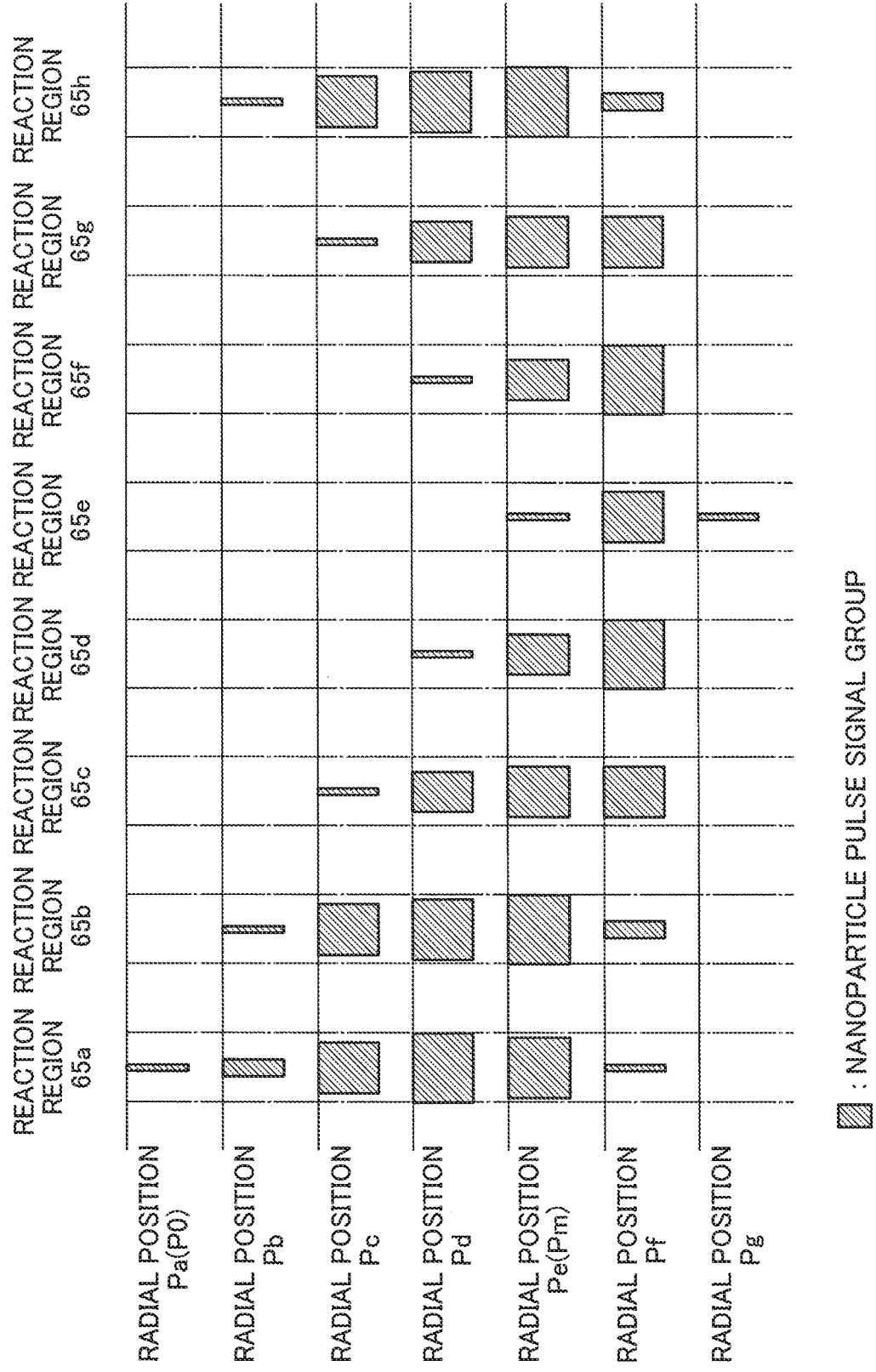
FIG. 15 is a schematic view for describing a relationship between the respective radial positions and a time width of the nanoparticle pulse signal group in the respective reaction regions.

FIG. 15 is a schematic view for describing a relationship between the respective radial positions Pa to Pg and a time width of the nanoparticle pulse signal group MS in the respective reaction regions 65a to 65h. The hatched regions each schematically indicate the nanoparticle pulse signal group MS.

As shown in FIG. 15, the width of the nanoparticle pulse signal group in each reaction region varies depending on the radial positions. The width of the nanoparticle pulse signal group in each radial position varies depending on the reaction regions.

Therefore, the controller 9 generates as appropriate measurement gate signals GSa_n to GSh_n respectively having pulse widths WGa_n to WGh_n (refer to (e) of FIG. 12) each slightly greater than the time width of the nanoparticle pulse signal group MS (refer to (a) of FIG. 12) in the respective reaction regions 65a to 65h, while associating the radial positions scanned with the laser light 20a with the respective reaction regions 65a to 65h.

In particular, as shown in FIG. 11, a locus LSa of the laser light 20a at the radial position Pa (n=a) only passes through the reaction region 65a. The controller 9 thus generates a measurement gate signal GSa_a (n=a) having a pulse width WGa_a (n=a) slightly greater than the time width of the nanoparticle pulse signal group MS in the reaction region 65a shown in FIG. 15. The radial position Pa corresponds to the radial position P0.

A locus LSb of the laser light 20a at the radial position Pb (n=b) passes through the three reaction regions 65a, 65b, and 65h. The controller 9 thus generates measurement gate signals GSa_b, GSb_b, and GSh_b (n=b) respectively having pulse widths WGa_b, WGb_b, and WGh_b (n=b) slightly greater than the time width of the nanoparticle pulse signal group MS in the respective reaction regions 65a, 65b, and 65h shown in FIG. 15.

A locus LSc of the laser light 20a at the radial position Pc (n=c) passes through the five reaction regions 65a, 65b, 65c, 65g, and 65h. The controller 9 thus generates measurement gate signals GSa_c, GSb_c, GSc_c, GSg_c, and GSh_c (n=c) respectively having pulse widths WGa_c, WGb_c, WGc_c, WGg_c, and WGh_c (n=c) slightly greater than the time width of the nanoparticle pulse signal group MS in the respective reaction regions 65a, 65b, 65c, 65g, and 65h shown in FIG. 15.

A locus LSd of the laser light 20a at the radial position Pd (n=d) passes through the seven reaction regions 65a, 65b, 65c, 65d, 65f, 65g, and 65h. The controller 9 thus generates measurement gate signals GSa_d, GSb_d, GSc_d, GSd_d, GSf_d, GSg_d, and GSh_d (n=d) respectively having pulse widths WGa_d, WGb_d, WGc_d, WGd_d, WGf_d, WGg_d, and WGh_d (n=d) slightly greater than the time width of the nanoparticle pulse signal group MS in the respective reaction regions 65a, 65b, 65c, 65d, 65f, 65g, and 65h shown in FIG. 15.

A locus LSe and LSf of the laser light 20a at the radial position Pe (n=e) and the radial position Pf (n=f) passes through all of the reaction regions 65a to 65h. The controller 9 thus generates measurement gate signals GSa_e to GSh_e (n=e) respectively having pulse widths WGa_e to WGh_e (n=e) and measurement gate signals GSa_f to GSh_f (n=f) respectively having pulse widths WGa_f to WGh_f (n=f) slightly greater than the time width of the nanoparticle pulse signal group MS in the respective reaction regions 65a to 65h shown in FIG. 15.

A locus LSg of the laser light 20a at the radial position Pg (n=g) only passes through the reaction region 65e. The controller 9 thus generates a measurement gate signal GSa_g (n=g) having a pulse width WGa_g (n=g) slightly greater than the time width of the nanoparticle pulse signal group MS in the reaction region 65e shown in FIG. 15.

Accordingly, the controller 9 generates, as appropriate, in step S13 the measurement gate signals GSa_n to GSh_n respectively having the pulse widths WGa_n to WGh_n each slightly greater than the time width of the nanoparticle pulse signal group MS in the respective reaction regions 65a to 65h, while associating the radial positions scanned with the laser light 20a with the respective reaction regions 65a to 65h. The controller 9 counts the number of the pulses of the nanoparticle pulse signal group MS in the respective measurement gate signals GSa_n to GSh_n, and adds the counted number in each track (n=0, 1, 2, . . . ) together.

The pulse widths WGa_n to WGh_n of the measurement gate signals GSa_n to GSh_n are preliminarily stored in the controller 9 in association with the radial position Pn in the respective reaction regions 65a to 65h.

The total number of the nanoparticles 82 in the respective reaction regions 65a to 65h thus can be measured such that the number of the pulses of the nanoparticle pulse signal group MS in the respective reaction regions 65a to 65h is counted in each track (n=0, 1, 2, . . . ) and added together. The measurement of the number of the nanoparticles 82 can lead to the indirect measurement of the particular antigens 80 associated with a disease.

When the optical pickup 20 is moved from the inner side to the outer side of the substrate 60 while the substrate 60 is being rotated, the locus LSf of the laser light 20a is out of the reaction region 65a at the radial position Pf shown in FIG. 11. This hinders the continuous measurement on the basis of the envelope curve pulse signal ESa_n in the reaction region 65a.

In view of this, in step S14, the controller 9 shifts a target for measurement to the reaction region 65e most distant from the center Ca of the substrate 60 when the optical pickup 20 is moved to the radial position Pm (corresponding to the radial position Pe in FIG. 11) in front of the locus of the laser light 20a which is out of the reaction region 65a.

Figure 16A:
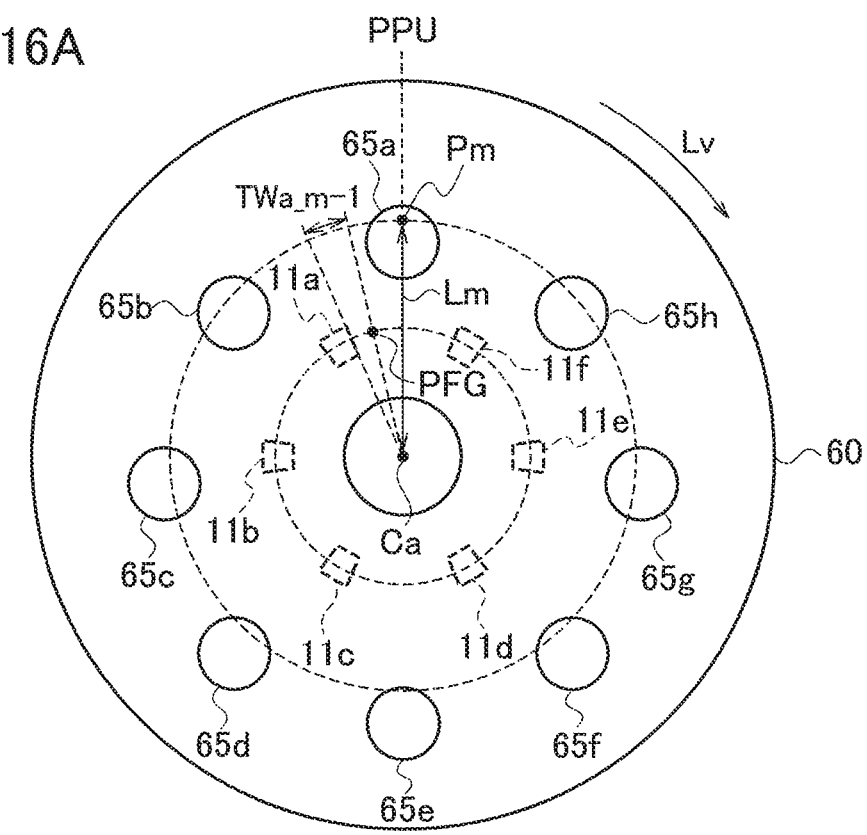
FIGS. 16A and 16B are schematic top views for describing a positional relationship between the respective reaction regions and the detecting position of the optical pickup when the optical pickup moves to a radial position Pm and a positional relationship between the respective FG elements and the detecting position of the turntable rotation detecting sensor.
Figure 16B:
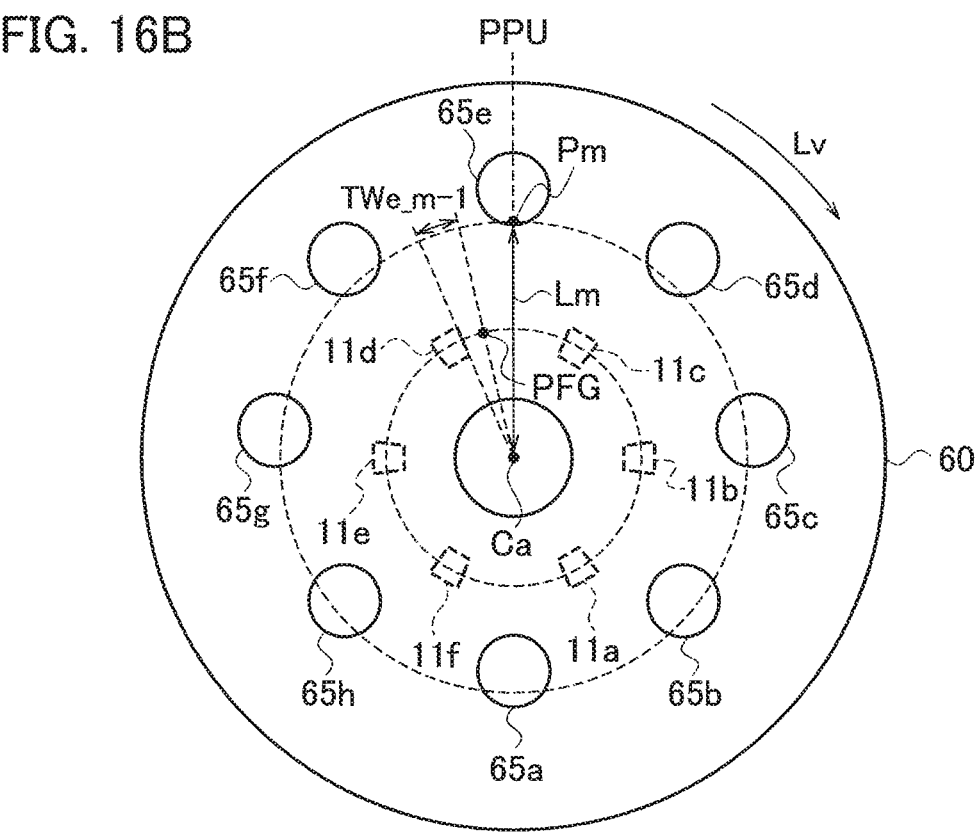

FIG. 16A illustrates a state in which the optical pickup 20 is moved to the radial position Pm and the reaction region 65a is moved to the detecting position PPU. FIG. 16B illustrates a state in which the substrate 60 is rotated from the state shown in FIG. 16A and the reaction region 65e is moved to the detecting position PPU at the radial position Pm. FIG. 16A and FIG. 16B each correspond to FIG. 11.

Figure 17:
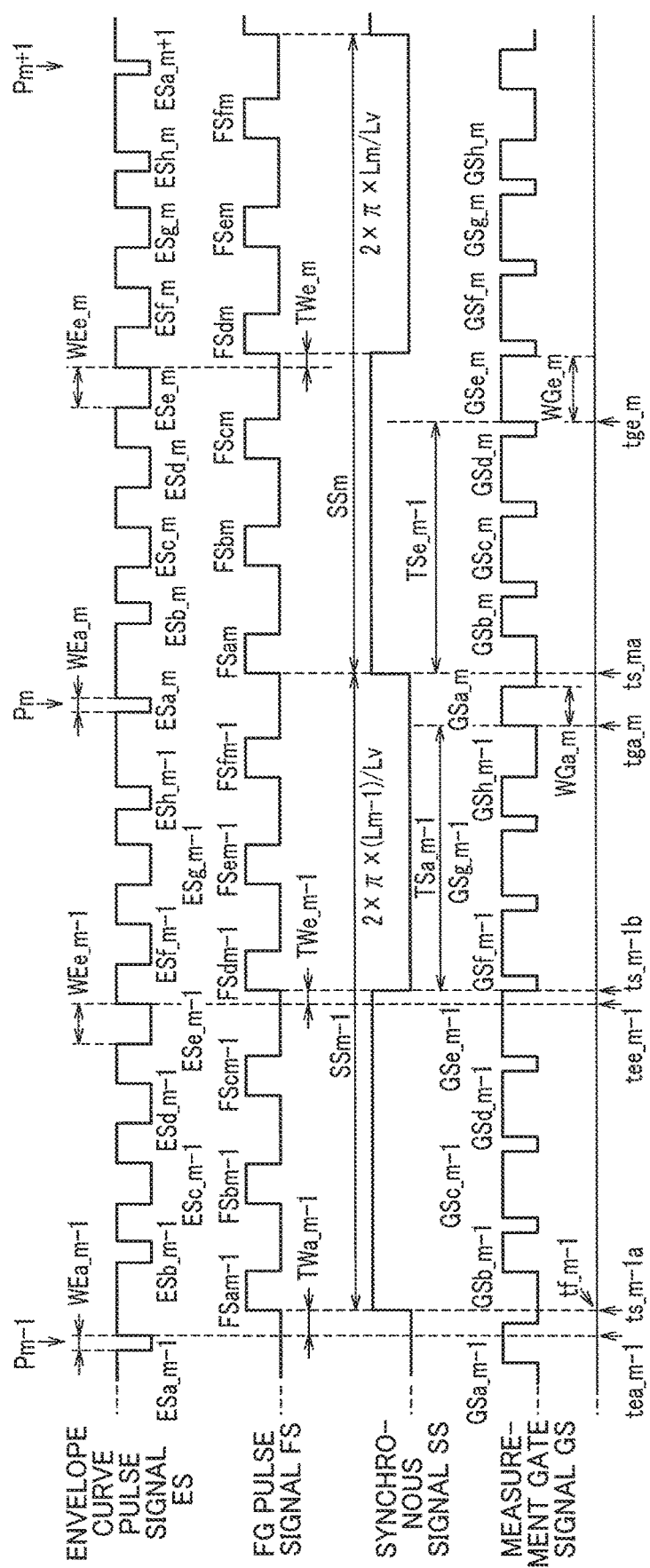
FIG. 17 is a time chart showing a relationship among the envelope curve pulse signal, the FG pulse signal, the synchronous signal, and the measurement gate signal.

FIG. 17 is a time chart showing a relationship among the envelope curve pulse signal ES, the FG pulse signal FS, the synchronous signal SS, and the measurement gate signal GS. FIG. 17 corresponds to FIG. 14.

In step S14, the controller 9 recognizes that the optical pickup 20 is moved to the radial position Pm (n=m) according to the positional information signal PS output from the optical pickup drive circuit 8 (refer to FIG. 6), so as to generate measurement gate signals GSa_m, GSb_m, GSc_m, GSd_m, GSe_m, GSf_m, GSg_m, and GSh_m respectively corresponding to the reaction regions 65a, 65b, 65c, 65d, 65e, 65f, 65g, and 65h. Since all of the reaction regions 65a to 65h are scanned at the radial position Pm, the measurement gate signals GSa_m to GSh_m corresponding to the reaction regions 65a to 65h are thus generated.

As shown in FIG. 17, the measurement gate signals GSa_m to GSd_m (n=m) are generated on the basis of the envelope curve pulse signal ESa_m−1 (n=m−1) in the reaction region 65a before the substrate 60 makes one revolution, as in the case described above.

In particular, the rising point of the measurement gate signal GSa_m (n=m) is set to the time tga_m after a lapse of a time period TSa_m−1 starting from a falling point (time ts_m−1b) of the synchronous signal SSm−1 and calculated according to Equation (2). The rising points of the measurement gate signals GSb_m to GSd_m (n=m) are also set in the same manner.

The measurement gate signal GSe_m (n=m) is generated on the basis of the envelope curve pulse signal ESe_m−1 (n=m−1) in the reaction region 65e before the substrate 60 makes one revolution.

In particular, the rising point of the measurement gate signal GSe_m is set to the time tge_m after a lapse of a time period TSe_m−1 starting from a rising point (time ts_ma) of the synchronous signal SSm and calculated according to the following Equation (3). The rising points of the following measurement gate signals after the measurement gate signal GSe_m are also set in the same manner.

$$TSe\_m-1 = \frac{\pi \times Lm}{Lv} - \left(\frac{WEe\_m-1}{2} + TWe\_m-1 + \frac{WGe\_m}{2}\right) \quad (3)$$

In Equation (3), Lm (n=m) is a distance from the center Ca of the substrate 60 to the radial position Pm (corresponding to the radial position Pe in FIG. 11), WEe_m−1 is a pulse width of the envelope curve pulse signal ESe_m−1 in the reaction region 65e detected by the measurement gate signal GSe_m−1 at the radial position Pm−1, TWe_m−1 is a period from the rising time tee_m−1 of the envelope curve pulse signal ESe_m−1 to the falling time ts_m−1b of the synchronous signal SSm−1, and WGe_m is a pulse width of the measurement gate signal GSe_m at the radial position Pm.

The controller 9 thus generates the measurement gate signals GSa_m to GSh_m synchronous with the envelope curve pulse signals ESa_m to ESh_m.

Accordingly, the measurement can be continued such that the reaction region as a target for measurement is shifted depending on the radial position Pm scanned with the laser light 20a.

The controller 9 keeps counting the number of pulses of the nanoparticle pulse signal group MS in the respective reaction regions 65a to 65h after the reaction region 65a is shifted to the reaction region 65e as a target for measurement, and adds the counted number in each track together.

In step S15, the controller 9 recognizes that the measurement in the respective reaction regions 65a to 65h is finished according to the positional information signal PS output from the optical pickup drive circuit 8.

In step S16, the controller 9 controls the optical pickup drive circuit 8 to move the optical pickup 20 to the initial position and stop the emission of the laser light 20a. The controller 9 controls the turntable drive circuit 4 to stop the rotation of the turntable 10.

Figure 18:
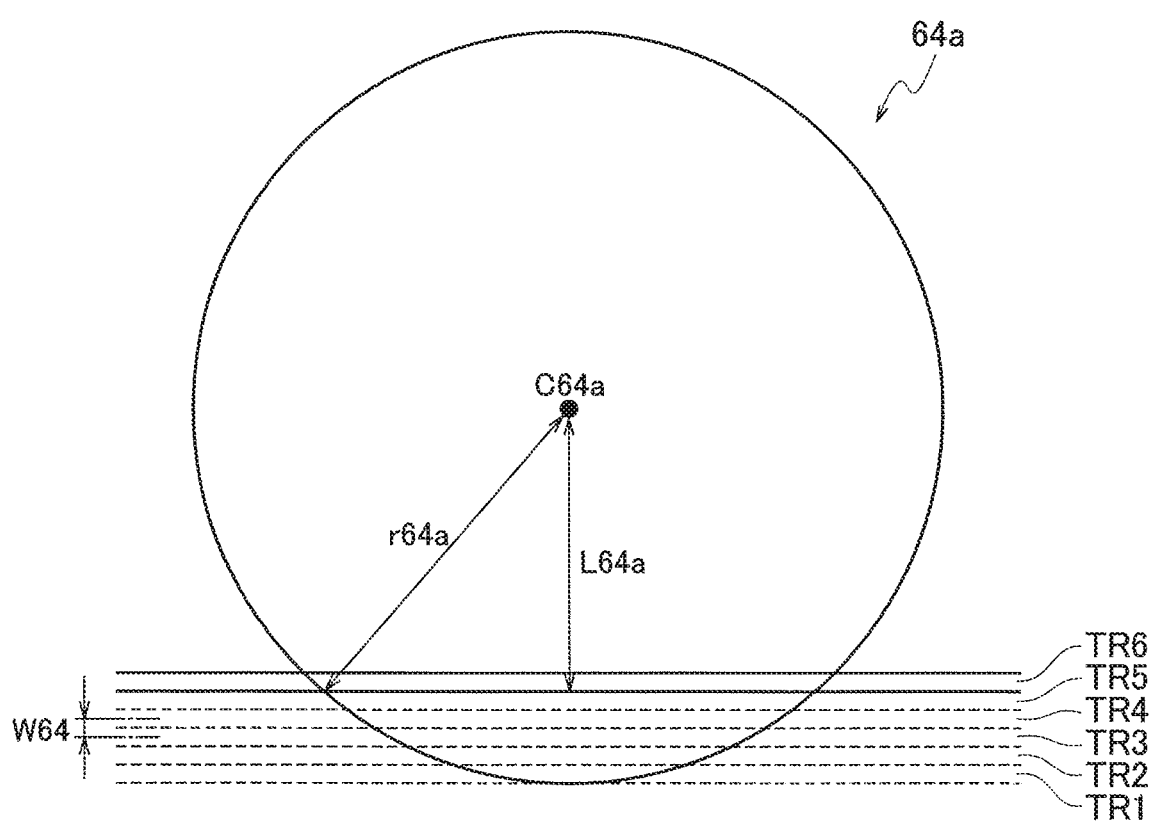
FIG. 18 is a schematic view for describing a method of complementing the total number of nanoparticles in the reaction region.

FIG. 18 is a schematic view for describing a method of complementing the total number of the nanoparticles 82 (pulses) in the reaction region 65a.

FIG. 18 illustrates a state in which the laser light 20a scans the respective tracks TR1 to TR6 from right to left. The controller 9 determines whether or not the pulse width WEa_n of the envelope curve pulse signal ESa_n in the reaction region 65a is greater than or equal to the predetermined pulse width Wth in step S8. FIG. 18 illustrates a case in which the pulse width WEa_n is determined not to be greater than or equal to the predetermined pulse width Wth (NO) in the tracks TR1 to TR5, and the pulse width WEa_n is determined to be greater than or equal to the predetermined pulse width Wth (YES) when the laser light 20a scans the track TR6.

In this case, while the number of the nanoparticles 82 (pulses) can be counted in the track TR6 and the following tracks, the number of the nanoparticles 82 are not counted in the tracks TR1 to TR5.

Thus, the number of the nanoparticles 82 (pulses) in the tracks TR1 to TR5 in which the nanoparticles 82 are not counted is complemented, so as to normalize the total number of the nanoparticles 82 in the reaction region 65a.

In particular, the number of the nanoparticles 82 in the tracks TR1 to TR5 is complemented according to a ratio of the area of the tracks TR1 to TR5 in which the nanoparticles 82 (pulses) are not counted to the area of the track TR6 and the following tracks in which the nanoparticles 82 (pulses) are counted, so as to normalize the total number of the nanoparticles 82 in the reaction region 65a. The track from which the nanoparticles 82 are counted first can be specified such that the radial position PS (n=s) is specified according to the positional information signal PS output from the optical pickup drive circuit 8.

For example, when the radius r64a of the reaction region 65a is set to 3 mm and the track pitch W64 is set to 320 nm, the distance L64a from the center C64a of the reaction region 65a to the track TR5 is 2.9984 mm. The area in which the nanoparticles 82 are counted is 28.274125 square millimeters, and a complemented ratio of the total area of the reaction region 65a (28.274334) to the area in which the nanoparticles 82 are counted thus results in 1.0000074.

Accordingly, the total number of the nanoparticles 82 in the reaction region 65a can be normalized such that the total number of the nanoparticles 82 counted in the track TR6 and the following tracks is multiplied by the complemented ratio obtained above.

Therefore, in step S17, the controller 9 complements the number of the nanoparticles 82 (pulses) in the tracks in which the nanoparticles 82 are not counted in the reaction region 65a according to the radial position Ps (n=s) specified in step S8, so as to normalize the total number of the nanoparticles 82 in the reaction region 65a.

The normalization of the total number of the nanoparticles 82 can be applied to the other reaction regions 65b to 65h.

The number of the nanoparticles 82 in the respective reaction regions 65b to 65h is stored in the analysis device 1 or output to the outside of the analysis device 1.

In accordance with the analysis device 1 and the analysis method according to a first embodiment, the substrate 60 is held such that the plurality of reaction regions 65 are located on the circumference 72 of the circle having the center Cb at a position different from the rotation axis C10 of the turntable 10 (the position separated by the predetermined distance Lx from the center Ca of the substrate 60). The determination of the reaction region detected first can sequentially specify the following reaction regions due to a time lag in the detection of the plurality of reaction regions 65.

The analysis device 1 and the analysis method according to a first embodiment thus can specify the respective reaction regions even when the positional information about the reaction regions is not recorded on the substrate so as to analyze biomaterials such as antibodies and antigens.

The analysis device 1 and the analysis method according to a first embodiment generates the measurement gate signal for extracting the nanoparticle pulse signal group from the light reception level signal in each reaction region depending on the detecting position of the optical pickup, in accordance with the turntable rotation detecting signal output from the turntable rotation detecting sensor, the synchronous signal in which the turntable rotation detecting signal is divided into frequencies, and the envelope curve pulse signal generated according to the light reception level signal output from the optical pickup.

Accordingly, the nanoparticle pulse signal group to be detected can be extracted with noise excluded, so as to improve the accuracy of detecting the nanoparticles to be analyzed.

Second Embodiment

An analysis device and an analysis method according to a second embodiment are described below with reference to FIG. 19A to FIG. 28. The same elements as in a first embodiment are indicated by the same reference numerals for illustration purposes.

[Reaction Regions of Substrate]

Figure 19A:
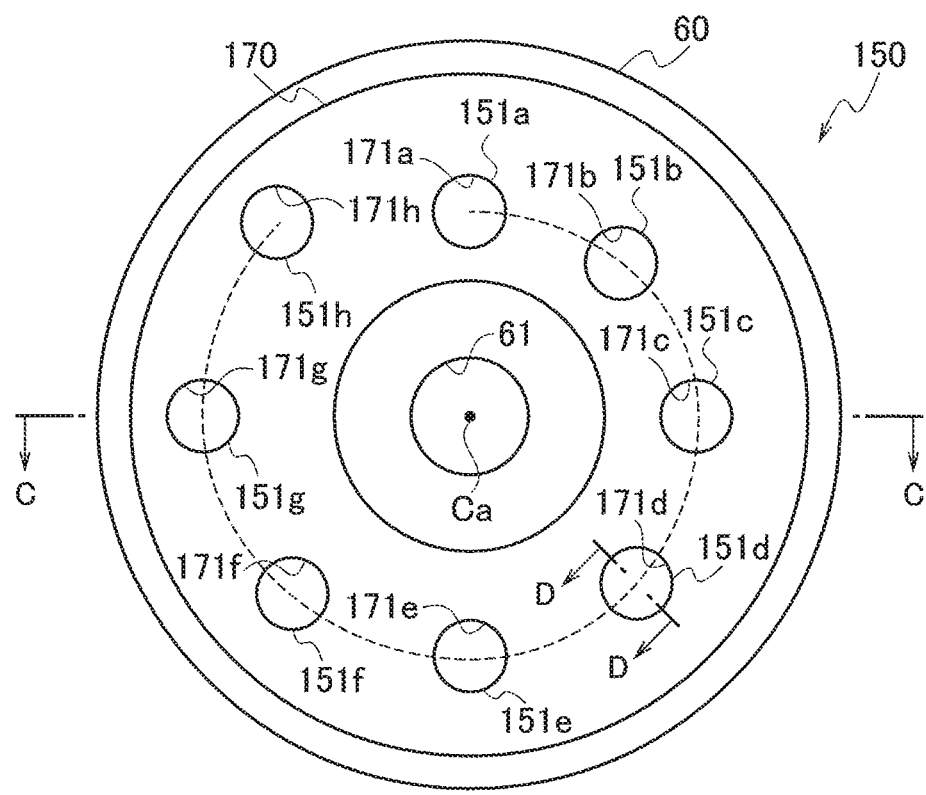
FIG. 19A is a schematic top view of an antigen capture unit according to a second embodiment.
Figure 19B:
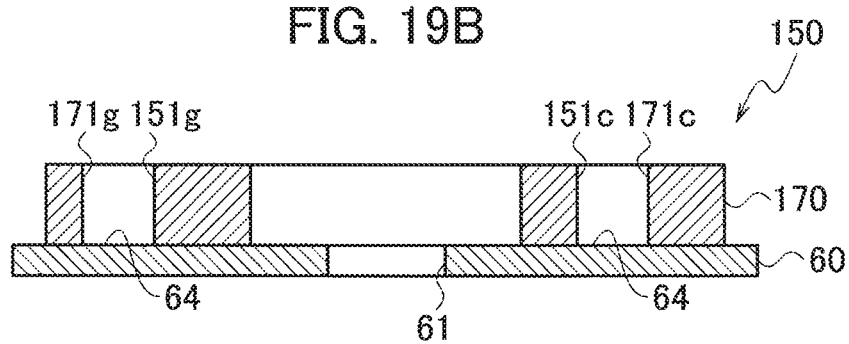
FIG. 19B is a schematic cross-sectional view taken along line C-C in FIG. 19A.
Figure 19C:
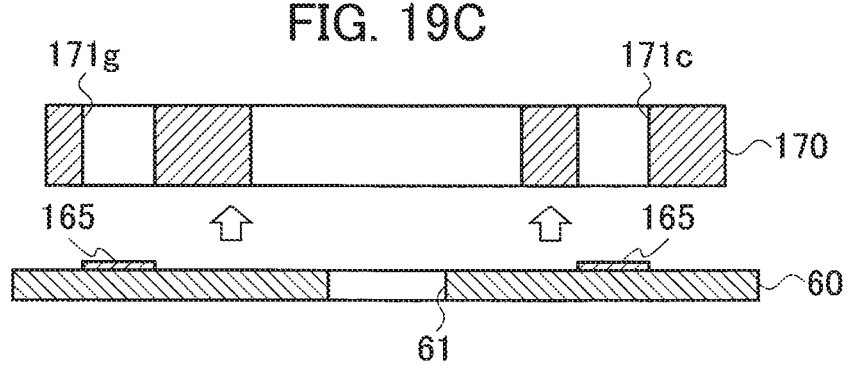
FIG. 19C is a schematic cross-sectional view illustrating a cartridge which is detachable from a substrate.

Reaction regions of a substrate are described with reference to FIGS. 19A-19C and FIG. 20. FIG. 19A is a schematic top view of an antigen capture unit 150 for forming reaction regions 165 on the substrate 60 (shown in FIG. 19C). FIG. 19B is a schematic cross-sectional view taken along line C-C in FIG. 19A. FIG. 19C is a schematic cross-sectional view illustrating a cartridge 170 which is detachable from the substrate 60. FIG. 19C corresponds to FIG. 19B.

The antigen capture unit 150 in a second embodiment differs from the antigen capture unit 50 in a first embodiment in the position of the penetration holes of the cartridge. The position of the respective reaction regions formed by the antigen capture unit in a second embodiment thus differs from that in a first embodiment.

As shown in FIG. 19A and FIG. 19B, the antigen capture unit 150 includes the substrate 60 and the cartridge 170. The substrate 60 in a second embodiment is common to the substrate 60 in a first embodiment. The surface of the substrate 60 thus includes the track regions 64 provided with the convex regions 62 and the recesses 63 alternately arranged in the radial direction, as shown in FIG. 2. The convex regions 62 and the recesses 63 are formed in a spiral from the inner side to the outer side of the substrate 60.

As shown in FIG. 19A, the cartridge 170 has a ring-like shape. The cartridge 170 is provided with a plurality of cylindrical penetration holes 171 formed in a spiral in the same direction as the spiral direction of the convex regions 62 and the recesses 63. The respective penetration holes 171 are indicated with adscripts "a" to "h" sequentially in the spiral direction from the inner side to the outer side of the substrate 60 for illustration purposes; namely, the cartridge 170 includes a first penetration hole 171a, a second penetration hole 171b, a third penetration hole 171c, a fourth penetration hole 171d, a fifth penetration hole 171e, a sixth penetration hole 171f, a seventh penetration hole 171g, and an eighth penetration hole 171h. The penetration holes 171a to 171h are arranged such that the first penetration hole 171a is located on the inner side, sequentially followed by the second penetration hole 171b, the third penetration hole 171c, the fourth penetration hole 171d, the fifth penetration hole 171e, the sixth penetration hole 171f, the seventh penetration hole 171g, and the eighth penetration hole 171h so as to gradually approach the outer side of the substrate 60 in the clockwise direction.

As shown in FIG. 19B and FIG. 2, the antigen capture unit 150 includes a plurality of wells 151 defined by the penetration holes 171 of the cartridge 170 and the track regions 64 of the substrate 60. The inner surface of the penetration holes 171 corresponds to the inner surface of the wells 151, and the track regions 64 of the substrate 60 corresponds to the bottoms of the wells 151. The wells 151 each serve as a holder for storing a solution such as a sample solution or a buffer solution.

The plurality of wells 151 correspond to the respective penetration holes 171. The wells 151 are thus formed in a spiral in the same direction as the spiral direction of the convex regions 62 and the recesses 63. The respective wells 151 are indicated with adscripts "a" to "h" sequentially in the spiral direction from the inner side to the outer side of the substrate 60 for illustration purposes; namely, the antigen capture unit 150 includes a first well 151a, a second well 151b, a third well 151c, a fourth well 151d, a fifth well 151e, a sixth well 151f, a seventh well 151g, and an eighth well 151h, corresponding to the penetration holes 171a to 171h. The wells 151a to 151h are arranged such that the first well 151a is located on the inner side, sequentially followed by the second well 151b, the third well 151c, the fourth well 151d, the fifth well 151e, the sixth well 151f, and the seventh well 151h so as to gradually approach the outer side of the substrate 60 in the clockwise direction.

Although FIG. 19A illustrates the antigen capture unit 150 including eight wells 151, the number of wells 151 is not limited to eight.

As shown in FIG. 3, when a buffer solution including the antibodies 81 which specifically bind to the antigens 80, which is specific protein, is injected into the wells 151, the antibodies 81 are fixed to the track regions 64 as solid-phase antibodies. Hereinafter, the antibodies 81 are referred to as solid-phase antibodies 81.

When a sample solution including the antigens 80 is injected into the wells 151, the antigens 80 are specifically bound to the solid-phase antibodies 81 and captured on the track regions 64, more particularly, captured on the recesses 63.

When a buffers solution including the nanoparticles 82 to which antibodies specifically binding to the antigens 80 are fixed is injected into the wells 151, the nanoparticles 82 to be analyzed specifically bind to the antigens 80 captured on the recesses 63 in the track regions 64 so as to be captured on the recesses 63 as labeling antibodies. Accordingly, the antigens 80 are captured and sandwiched between the solid-phase antibodies 81 and the nanoparticles 82 as labeling antibodies on the recesses 63 in the track regions 64.

As shown in FIG. 19C, the cartridge 170 is detachable from the substrate 60. The nanoparticles 82 are detected only by use of the substrate 60 detached from the cartridge 170.

Figure 20:
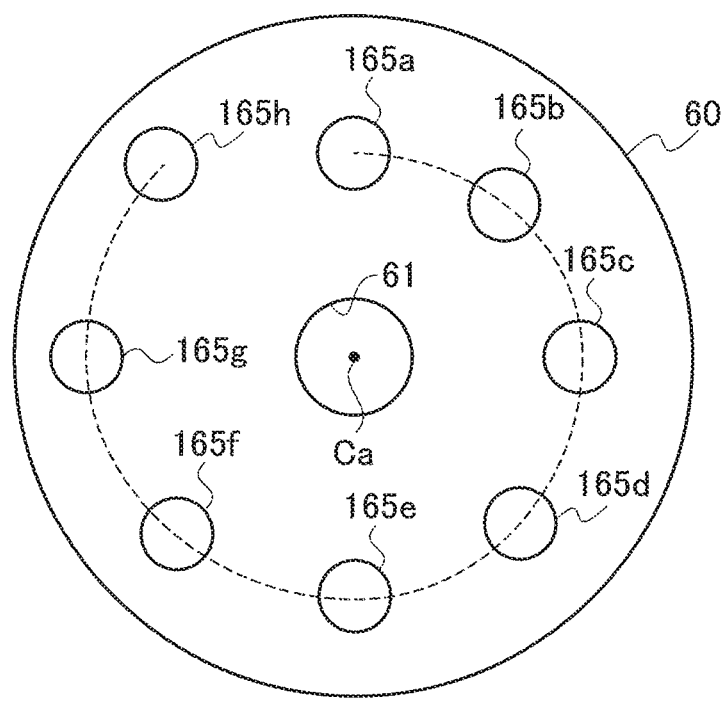
FIG. 20 is a schematic top view of a substrate including reaction regions formed by use of the antigen capture unit according to a second embodiment.

FIG. 20 is a schematic view of the substrate 60 including the reaction regions 165 formed by use of the antigen capture unit 150.

The track regions 64 corresponding to the bottoms of the wells 151 on the substrate 60 serve as the respective reaction regions 165 on which the antigens 80 and the nanoparticles 82 are captured by an antigen-antibody reaction. The substrate 60 is thus provided with the plurality of reaction regions 165 for capturing the nanoparticles 82 to be analyzed, corresponding to the respective wells 151. The reaction regions 165 are thus formed in a spiral in the same direction as the spiral direction of the convex regions 62 and the recesses 63.

The respective reaction regions 165 are indicated with adscripts "a" to "h" sequentially in the spiral direction from the inner side to the outer side of the substrate 60 for illustration purposes; namely, the substrate 60 includes a first reaction region 165a, a second reaction region 165b, a third reaction region 165c, a fourth reaction region 165d, a fifth reaction region 165e, a sixth reaction region 165f, a seventh reaction region 165g, and an eighth reaction region 165h, corresponding to the respective wells 151a to 151h.

The reaction regions 165a to 165h are arranged such that the first reaction region 165a is located on the inner side, sequentially followed by the second reaction region 165b, the third reaction region 165c, the fourth reaction region 165d, the fifth reaction region 165e, the sixth reaction region 165f, the seventh reaction region 165g, and the eighth reaction region 165h so as to gradually approach the outer side of the substrate 60 in the clockwise direction.

Although FIG. 20 illustrates the substrate 60 including eight reaction regions 165 corresponding to the eight wells 151, the number of reaction regions 165 is not limited to eight, as in the case of the wells 151.

[Analysis Device]

The analysis device according to a second embodiment is common to the analysis device 1 according to a first embodiment. The substrate 60 in a second embodiment held on the turntable 10 between the clamper 2 and the turntable 10 such that the center Ca of the substrate 60 is located on the rotation axis C10 of the turntable 10.

[Analysis Method]

The analysis method according to a second embodiment has substantially the same process as in a first embodiment, but differs in specific processing derived from the difference in the position of the respective reaction regions.

Figure 21A:
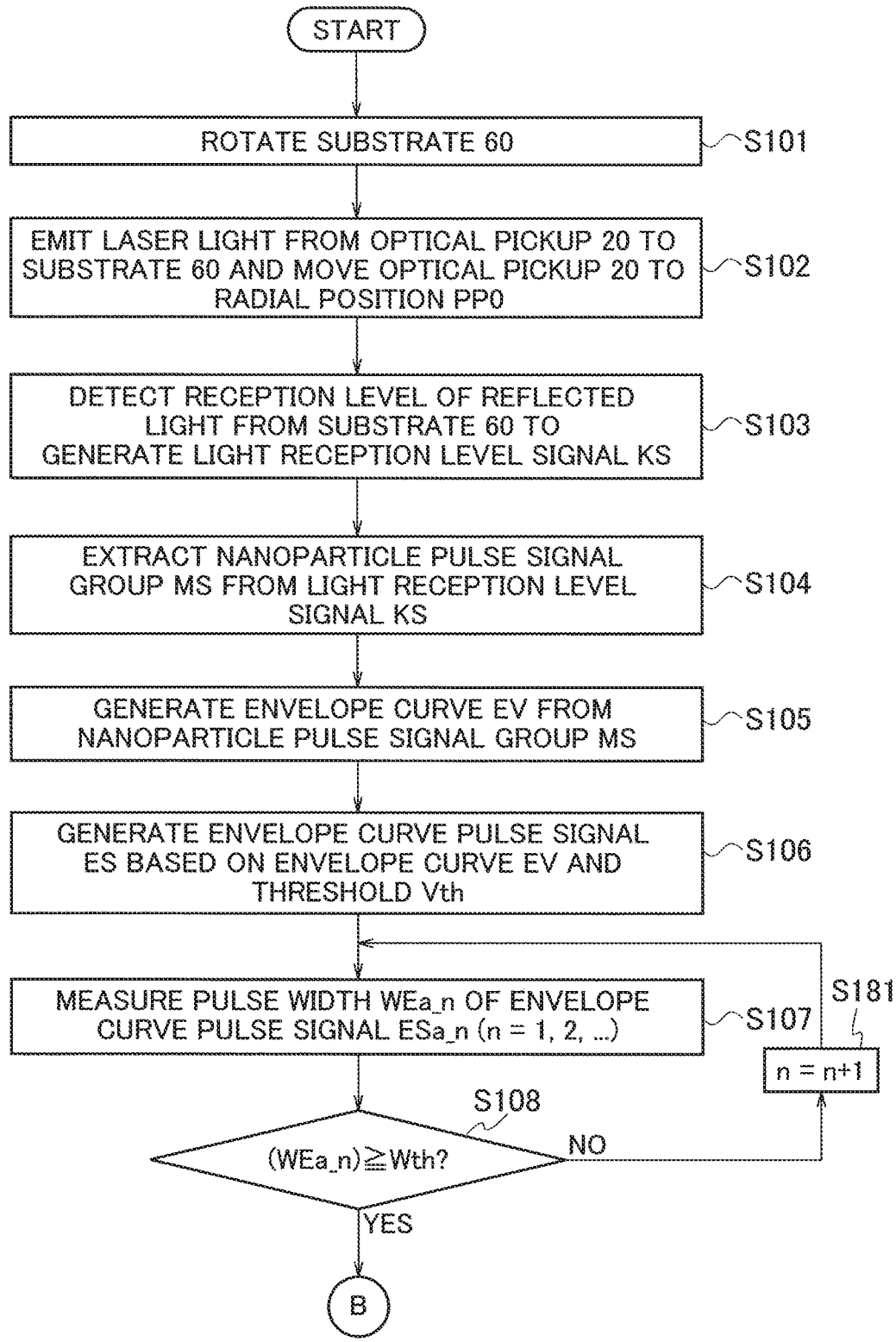
FIG. 21A is a flow chart for describing an analysis method according to a second embodiment.
Figure 21B:
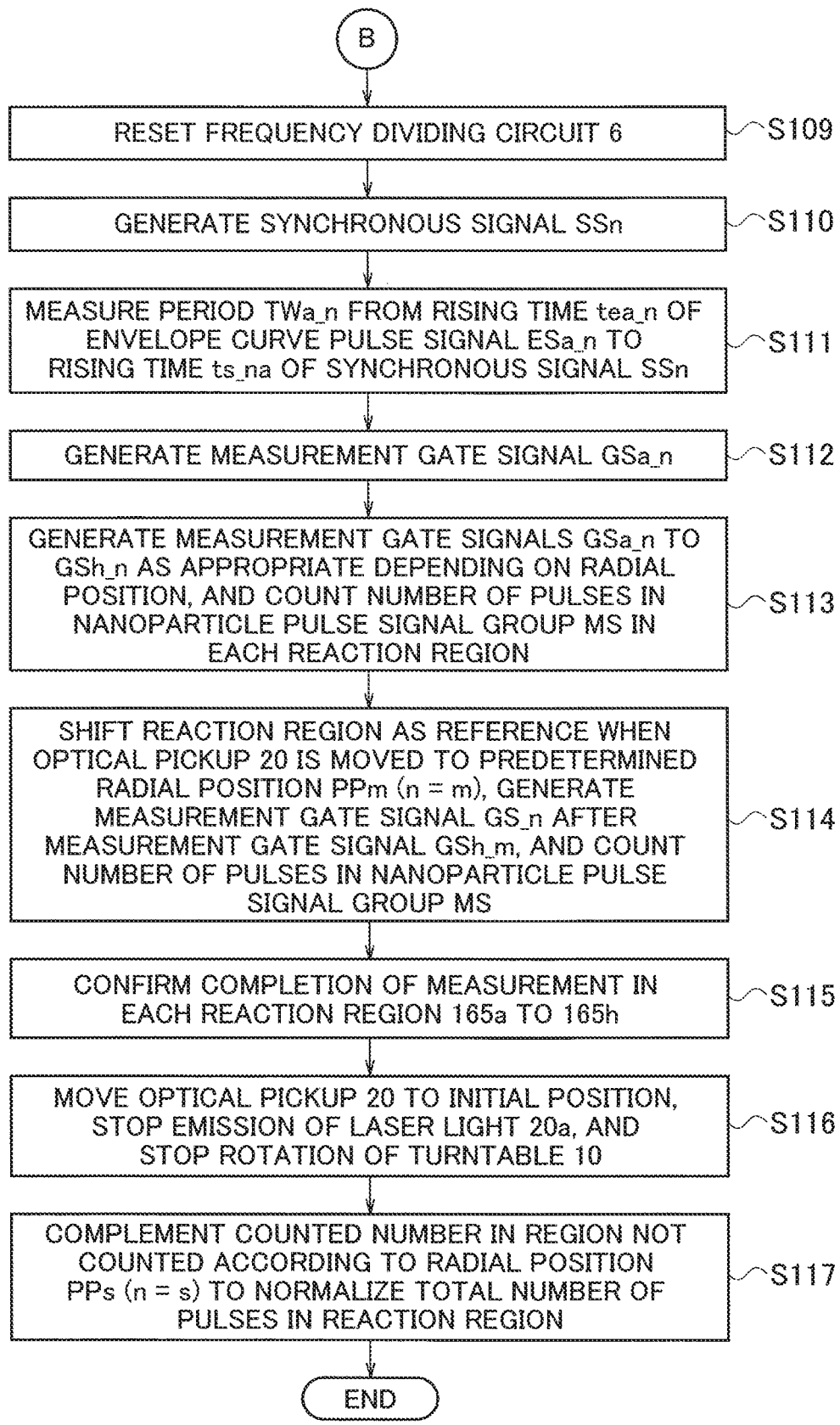
FIG. 21B is a flow chart for describing the analysis method according to a second embodiment.
Figure 22:
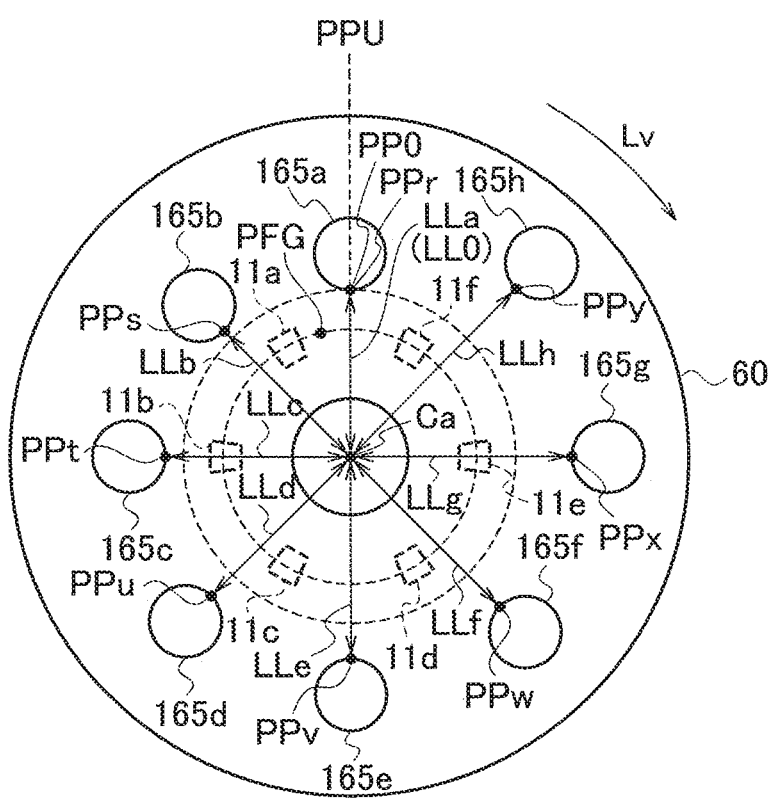
FIG. 22 is a schematic top view for describing a positional relationship between the respective reaction regions and a radial position corresponding to a detecting position of an optical pickup.

FIG. 21A and FIG. 21B are flow charts for describing a method of analyzing the nanoparticles 82 by the analysis device 1. FIG. 22 is a schematic top view for describing a positional relationship between the respective reaction regions 165a to 165h and a radial position PPn corresponding to the reception-level detecting position of the optical pickup 20. While FIG. 20 illustrates the substrate 60 as viewed from the side provided with the reaction regions 165, FIG. 22 illustrates the substrate 60 as viewed from the side opposite to the side provided with the reaction regions 165, namely, as viewed from the clamper 2 side. FIG. 23, FIG. 24, and FIGS. 27A and 27B also illustrate the substrate as viewed from the same side as FIG. 22.

The distance from the center Ca of the substrate 60 to the radial position PPr (n=r) of the first reaction region 165a at the edge toward the center Ca is defined as LLa. The distance from the center Ca of the substrate 60 to the radial position PPs (n=s) of the second reaction region 165b is defined as LLb. The distance from the center Ca of the substrate 60 to the radial position PPt (n=t) of the third reaction region 165c is defined as LLc. The distance from the center Ca of the substrate 60 to the radial position PPu (n=u) of the fourth reaction region 165d is defined as LLd. The distance from the center Ca of the substrate 60 to the radial position PPv (n=v) of the fifth reaction region 165e is defined as LLe. The distance from the center Ca of the substrate 60 to the radial position PPw (n=w) of the sixth reaction region 165f is defined as LLf. The distance from the center Ca of the substrate 60 to the radial position PPx (n=x) of the seventh reaction region 165g is defined as LLg. The distance from the center Ca of the substrate 60 to the radial position PPy (n=y) of the eighth reaction region 165h is defined as LLh.

The radial position PPn corresponds to the detecting position of the optical pickup 20 for detecting the respective reaction regions 165a to 165h. In particular, the radial position PPn is the reception-level detecting position on the detecting position PPU of the optical pickup 20 at which the optical pickup 20 emits the laser light 20a to the substrate 60 and receives the reflected light from the substrate 60. The radial position PPn is also a relative position based on the rotation axis C10 of the turntable 10 in the direction perpendicular to the rotation axis C10. The small letter "n" corresponds to the track number in the respective track regions 64.

The controller 9 can detect the radial position PPn according to the positional information signal PS output from the optical pickup drive circuit 8.

The respective distances LLa to LLh to the respective reaction regions 165a to 165h can be represented by the following relational expression: LLa<LLb<LLc<LLd<LLe<LLf<LLg<LLh.

In step S101 in FIG. 21A, the controller 9 controls the turntable drive circuit 4 to direct the turntable drive unit 3 to drive the turntable 2 so that the substrate 60 rotates at a constant linear velocity Lv.

In step S102, the controller 9 directs the optical pickup 20 to emit the laser light 20a to the substrate 60, and controls the optical pickup drive circuit 8 to move the optical pickup 20 to the radial position PP0 (n=0) at which the distance from the center C1 of the substrate 60 is LL0 (LLa=LL0<LLb). The distance LL0 is 24 mm, for example.

In step S103, the optical pickup 20 receives the reflected light from the substrate 60. The optical pickup 20 detects the reception level of the reflected light, generates a light reception level signal KS, and outputs the signal to the controller 9.

Figure 23:
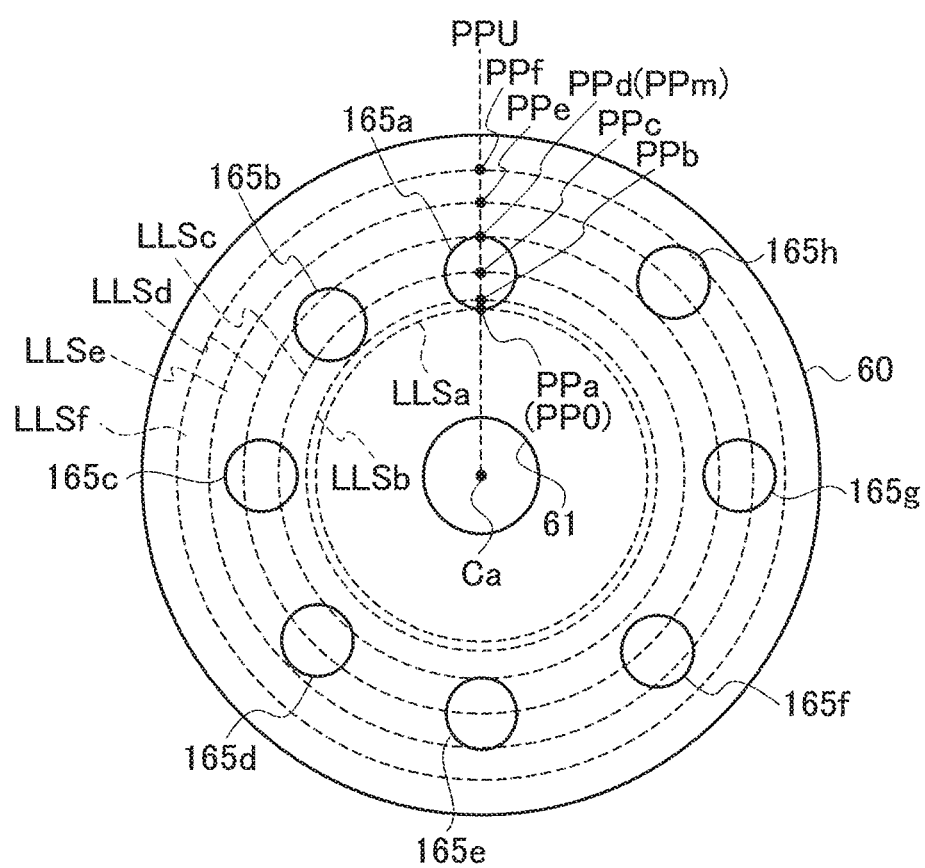
FIG. 23 is a schematic top view for describing a positional relationship between the respective reaction regions and the respective radial positions.

FIG. 23 is a schematic top view for describing a positional relationship between the respective reaction regions 165a to 165h and the respective radial positions PPa to PPf. The broken lines LLSa to LLSf in FIG. 23 schematically indicate loci obtained when the laser light 20a scans the respective radial positions PPa to PPf. The radial position PPa in FIG. 23 corresponds to the radial position PP0.

When the optical pickup 20 is moved to the radial position PP0 while the substrate 60 is being rotated, the laser light 20a scans the circumference of the circle passing through the radial position PP0. Since the reaction region 165a is located closer to the center Ca than the other reaction regions 165b to 165h, only the reaction region 165a is scanned with the laser light 20a at the radial position PP0.

The light reception level signal KS is thus output from the optical pickup 20 to the controller 9 when the reaction region 165a is scanned with the laser light 20a at the radial position PP0.

In step S104, the controller 9 subjects the light reception level signal KS to filter processing to extract the nanoparticle pulse signal group MS, as shown in (a) of FIG. 12.

In step S105, the controller 9 subjects the nanoparticle pulse signal group MS to envelope curve processing to generate the envelope curve EV, as shown in (b) of FIG. 12.

In step S106, the controller 9 generates the envelope curve pulse signal ES based on the envelope curve EV and a predetermined threshold Vth, as shown in (c) and (d) of FIG. 12.

In step S107, the controller 9 measures the pulse width WEa_n of the envelope curve pulse signal ESa_n in the reaction region 165a. The small letter "a" in the envelope curve pulse signal ESa_n and the pulse width WEa_n is the same adscript as in the reaction region 65a. The small letter "n" corresponds to the track number (n=0, 1, 2, . . . ).

In step S108, the controller 9 determines whether or not the pulse width WEa_n is greater than or equal to a predetermined pulse width Wth.

When the pulse width WEa_n is determined not to be greater than or equal to the predetermined pulse width Wth (NO), the controller 9 measures the pulse width WEa_n of the envelope curve pulse signal ESa_n in the reaction region 165a in the next track (n=n+1) after the substrate 60 makes one revolution in step 181.

When the pulse width WEa_n is determined to be greater than or equal to the predetermined pulse width Wth (YES), the controller 9 specifies the radial position PPs (n=s) at which the pulse width WEa_n is determined to be greater than or equal to the predetermined pulse width Wth. The controller 9 resets the frequency dividing circuit 6 in step S109 in FIG. 21B.

Figure 24:
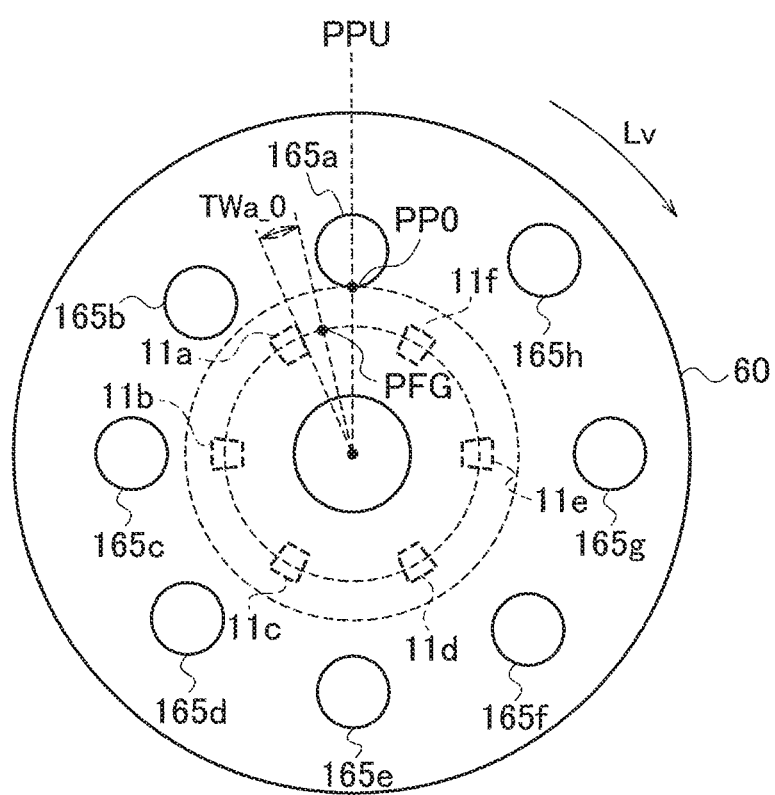
FIG. 24 is a schematic top view for describing a positional relationship between the respective reaction regions and the detecting position of the optical pickup when the optical pickup moves to a radial position PP0 and a positional relationship between FG elements and a detecting position of a turntable rotation detecting sensor.

FIG. 24 is a schematic top view for describing a positional relationship between the detecting position PPU of the optical pickup 20 and the respective reaction regions 165a to 165h when the optical pickup 20 is moved to the radial position PP0, and a positional relationship between the respective FG elements 11a to 11f and the detecting position PFG of the turntable rotation detecting sensor 5.

FIG. 24 illustrates the state in which the optical pickup 20 is moved to the radial position PP0, and the reaction region 165a is moved to the detecting position PPU.

Figure 25:
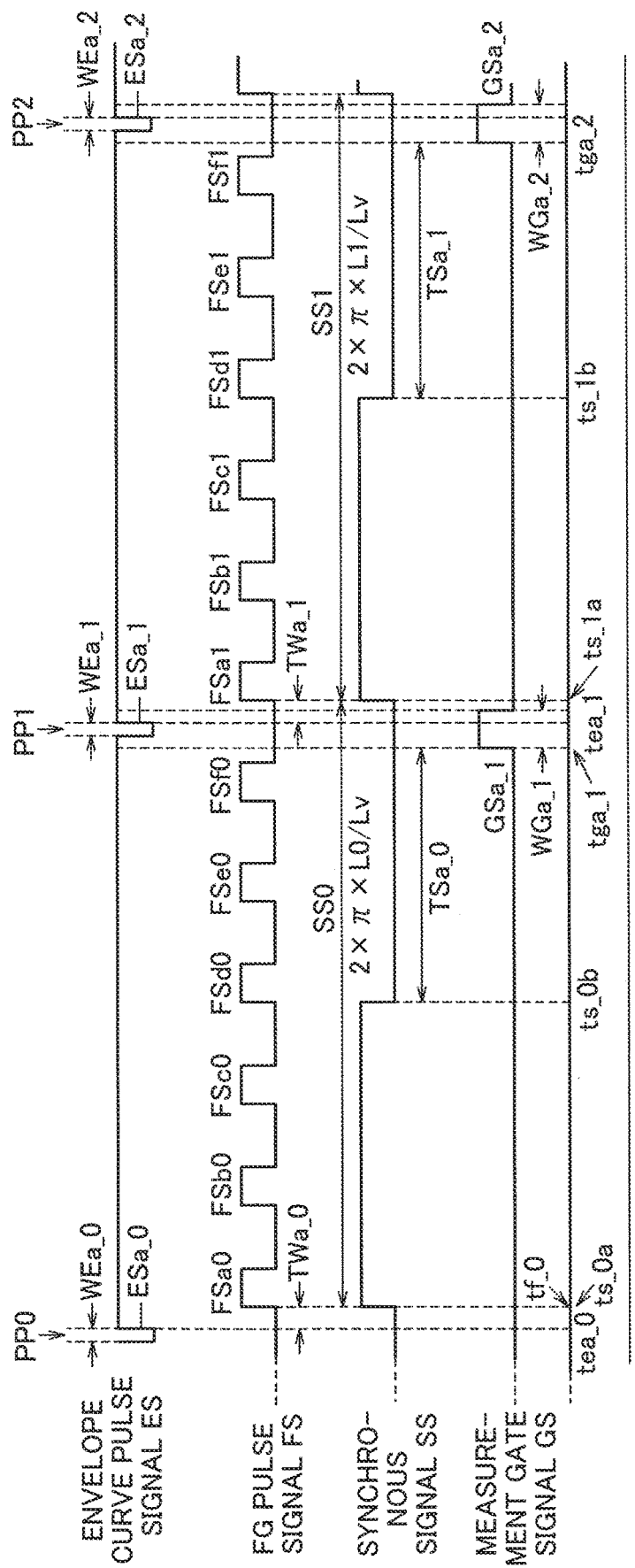
FIG. 25 is a time chart showing a relationship among an envelope curve pulse signal, an FG pulse signal, a synchronous signal, and a measurement gate signal.

FIG. 25 is a time chart showing the relationship among the envelope curve pulse signal ES, the FG pulse signal FS, the synchronous signal SS, and the measurement gate signal GS.

In the state shown in FIG. 24, when the pulse width WEa_0 (n=0) of the envelope curve pulse signal ESa_0 (n=0) shown in FIG. 25 is determined to be greater than or equal to the predetermined pulse width Wth (YES) in step S108, the controller 9 determines that the determined envelope curve pulse signal ESa_0 is the envelope curve pulse signal in the reaction region 165a in step S109.

Namely, the controller 9 specifies the reaction region 165*a* in accordance with the radial position PP0 and the envelope curve pulse signal ESa_0. The other reaction regions 165*b* to 165*h* are specified in association with the positional relation to the reaction region 165*a* accordingly.

The controller 9 defines the central position of the envelope curve pulse signal ESa_0 as a measurement reference, and resets the frequency dividing circuit 6 at the rising time tea_0 (n=0) of the envelope curve pulse signal ESa_0.

The reason for the determination as to whether the pulse width WEa_0 of the envelope curve pulse signal ESa_0 is greater than or equal to the predetermined pulse width Wth is to exclude noise from a target to be detected, as indicated by the region B1 shown in FIG. 10A, for example.

Typically, a pulse width of an envelope curve pulse signal generated from noise is narrower than the pulse width of the envelope curve pulse signal generated from the nanoparticle pulse signal group MS. Therefore, the envelope curve pulse signal as a target to be detected can only be extracted such that the pulse width of the envelope curve pulse signal is determined so as to exclude noise from a target to be detected.

In step S110, the frequency dividing circuit 6 generates a synchronous signal SS0 rising synchronously with a rising point (time tf_0) of an FG pulse signal FSa0 (n=0) which is input first after the reset, as shown in FIG. 25. The frequency dividing circuit 6 keeps generating the synchronous signal SSn (n=1, 2, . . . ) after generating the synchronous signal SS0 during the rotation of the substrate 60.

The synchronous signal SSn is obtained such that the FG pulse signal FS is subjected to frequency division by the frequency dividing circuit 6. The period of the synchronous signal SSn conforms to the rotation period of the substrate 60. Namely, when the number of the FG elements 11 is six as shown in FIG. 24, the frequency dividing circuit 6 generates the synchronous signal SSn in which the FG pulse signal FS is divided into six frequencies.

In step S111, the controller 9 measures a time period TWa_0 (n=0) from the rising time tea_0 of the envelope curve pulse signal ESa_0 to the rising time ts_0a (n=0) of the synchronous signal SS0.

In step S112, the controller 9 generates a measurement gate signal GSa_1 (n=1) for counting the number of pulses of the nanoparticle pulse signal group MS in the reaction region 165*a*. The measurement gate signal GSa_n corresponds to the measurement gate signal GS shown in FIGS. 10A and 10B and (e) of FIG. 12.

The track pitch W64 is 320 nm, for example. The distance L0 from the center Ca of the substrate 60 to the radial position PP0 is 24 mm, for example. The track pitch W64 is smaller by 0.0013% than the distance LL0. The period of the synchronous signal SSn from a point at which the reaction region 165*a* is detected at the radial position PP0 to a point at which the reaction region 165*a* is detected again after the substrate 60 makes one revolution, can be expressed by $2\times\pi\times LL0/Lv$ (n=0). The reference sign Lv is a velocity of rotation (a linear velocity) of the substrate 60.

The rising point of the measurement gate signal GSa_1 for counting the number of pulses of the nanoparticle pulse signal group MS in the reaction region 165*a* at the radial position PP1 after the substrate 60 makes one revolution from the radial position PP0, is set to the time tga_1 after a lapse of a time period TSa_0 starting from a falling point (time ts_0b) of the synchronous signal SS0 and calculated according to Equation (1). In Equation (1), WGa_1 (n=1) is a pulse width of the measurement gate signal GSa_1 at the radial position PP1. The pulse width WGa_n is preliminarily determined in association with the radial position PPn.

The rising point of the measurement gate signal GSa_2 at the radial position PP2 after the substrate 60 makes one revolution from the radial position PP1, is set to the time tga_2 after a lapse of a time period TSa_1 starting from a falling point (time ts_1b) of the synchronous signal SS1 (n=1). The time period TSa_1 is calculated in accordance with a pulse width WEa_1 (n=1), a time period TWa_1, and a pulse width WGa_2 (n=2) in the same manner as the time period calculated according to Equation (1).

The pulse width WEa_1 is a pulse width of the envelope curve pulse signal ESa_1 (n=1) in the reaction region 165*a* detected by the measurement gate signal GSa_1 at the radial position PP1. The time period TWa_1 is a period from the rising time tea_1 of the envelope curve pulse signal ESa_1 to the rising time ts_1a of the synchronous signal SS1. The pulse width WGa_2 (n=2) is a pulse width of the measurement gate signal GSa_2 (n=2) at the radial position PP2.

Therefore, the rising point of the measurement gate signal GSa_n is set to the time tga_n after a lapse of a time period TSa_n−1 starting from a falling point (time ts_n−1b) of the synchronous signal SSn−1 and calculated according to Equation (2).

The controller 9 thus generates the measurement gate signal GSa_n synchronous with the envelope curve pulse signal ESa_n.

In step S113, the controller 9 counts the number of pulses of the nanoparticle pulse signal group MS in the reaction region 165*a* in accordance with the light reception level signal KS detected in a predetermined period (the pulse width WGa_n) regulated by the measurement gate signal GSa_n, and adds the counted number in each track (n=0, 1, 2, . . . ) together.

The total number of the nanoparticles 82 in the reaction region 165*a* thus can be measured such that the number of the pulses of the nanoparticle pulse signal group MS in the reaction region 165*a* is counted in each track (n=0, 1, 2, . . . ) and added together. The measurement of the number of the nanoparticles 82 can lead to the indirect measurement of the particular antigens 80 associated with a disease.

FIG. 26 is a schematic view for describing a relationship between the respective radial positions PPa to PPf and a time width of the nanoparticle pulse signal group MS in the respective reaction regions 165*a* to 165*h*. The hatched regions each schematically indicate the nanoparticle pulse signal group MS.

As shown in FIG. 26, the width of the nanoparticle pulse signal group MS in each reaction region varies depending on the radial positions. The width of the nanoparticle pulse signal group MS in each radial position varies depending on the reaction regions.

Therefore, the controller 9 generates as appropriate measurement gate signals GSa_n to GSh_n respectively having pulse widths WGa_n to WGh_n (refer to (e) of FIG. 12) each slightly greater than the time width of the nanoparticle pulse signal group MS (refer to (a) of FIG. 12) in the respective reaction regions 165*a* to 165*h*, while associating the radial positions scanned with the laser light 20*a* with the respective reaction regions 165*a* to 165*h*.

In particular, as shown in FIG. 23, a locus LLSa of the laser light 20*a* at the radial position PPa (n=a) only passes through the reaction region 165*a*. The controller 9 thus generates a measurement gate signal GSa_a (n=a) having a pulse width WGa_a (n=a) slightly greater than the time width of the nanoparticle pulse signal group MS in the reaction region 165a shown in FIG. 26. The radial position PPa corresponds to the radial position PP0.

A locus LLSb of the laser light 20a at the radial position PPb (n=b) passes through the two reaction regions 165a and 165b. The controller 9 thus generates measurement gate signals GSa_b and GSb_b (n=b) respectively having pulse widths WGa_b and WGb_b (n=b) slightly greater than the time width of the nanoparticle pulse signal group MS in the respective reaction regions 165a and 165b shown in FIG. 26.

A locus LLSc of the laser light 20a at the radial position PPc (n=c) passes through the five reaction regions 165a, 165b, 165c, 165d, and 165e. The controller 9 thus generates measurement gate signals GSa_c, GSb_c, GSc_c, GSd_c, and GSe_c (n=c) respectively having pulse widths WGa_c, WGb_c, WGc_c, WGd_c, and WGe_c (n=c) slightly greater than the time width of the nanoparticle pulse signal group MS in the respective reaction regions 165a, 165b, 165c, 165d, and 165e shown in FIG. 26.

A locus LLSd of the laser light 20a at the radial position PPd (n=d) passes through all of the reaction regions 165a to 165h. The controller 9 thus generates measurement gate signals GSa_d to GSh_d (n=d) respectively having pulse widths WGa_d to WGh_d (n=d) slightly greater than the time width of the nanoparticle pulse signal group MS in the respective reaction regions 165a to 165h shown in FIG. 26.

A locus LLSe of the laser light 20a at the radial position PPe (n=e) passes through the four reaction regions 165e, 165f, 165g, and 165h. The controller 9 thus generates measurement gate signals GSe_e, GSf_e, GSg_e, and GSh_e (n=e) respectively having pulse widths WGe_e, WGf_e, WGg_e, and WGh_e (n=e) slightly greater than the time width of the nanoparticle pulse signal group MS in the respective reaction regions 165e, 165f, 165g, and 165h shown in FIG. 26.

A locus LLSf of the laser light 20a at the radial position PPf (n=f) only passes through the reaction region 165h. The controller 9 thus generates a measurement gate signal GSh_f (n=f) having a pulse width WGh_f (n=f) slightly greater than the time width of the nanoparticle pulse signal group MS in the reaction region 165h shown in FIG. 26.

Accordingly, the controller 9 generates, as appropriate, in step S113 the measurement gate signals GSa_n to GSh_n respectively having the pulse widths WGa_n to WGh_n each slightly greater than the time width of the nanoparticle pulse signal group MS in the respective reaction regions 165a to 165h, while associating the radial positions scanned with the laser light 20a with the respective reaction regions 165a to 165h.

The controller 9 counts the number of the pulses of the nanoparticle pulse signal group MS in the respective measurement gate signals GSa_n to GSh_n, and adds the counted number in each track (n=0, 1, 2, . . . ) together.

The pulse widths WGa_n to WGh_n of the measurement gate signals GSa_n to GSh_n are preliminarily stored in the controller 9 in association with the radial position PPn in the respective reaction regions 165a to 165h.

The total number of the nanoparticles 82 in the respective reaction regions 165a to 165h thus can be measured such that the number of the pulses of the nanoparticle pulse signal group MS in the respective reaction regions 165a to 165h is counted in each track (n=0, 1, 2, . . . ) and added together. The measurement of the number of the nanoparticles 82 can lead to the indirect measurement of the particular antigens 80 associated with a disease.

When the optical pickup 20 is moved from the inner side to the outer side of the substrate 60 while the substrate 60 is being rotated, the locus LLSe of the laser light 20a is out of the reaction region 165a at the radial position PPe shown in FIG. 23. This hinders the continuous measurement on the basis of the envelope curve pulse signal ESa_n in the reaction region 165a.

In view of this, in step S114, the controller 9 shifts a target for measurement to the reaction region 165h most distant from the center Ca of the substrate 60 when the optical pickup 20 is moved to the radial position PPm (corresponding to the radial position PPd in FIG. 23) in front of the locus of the laser light 20a which is out of the reaction region 165a.

Figure 27A:
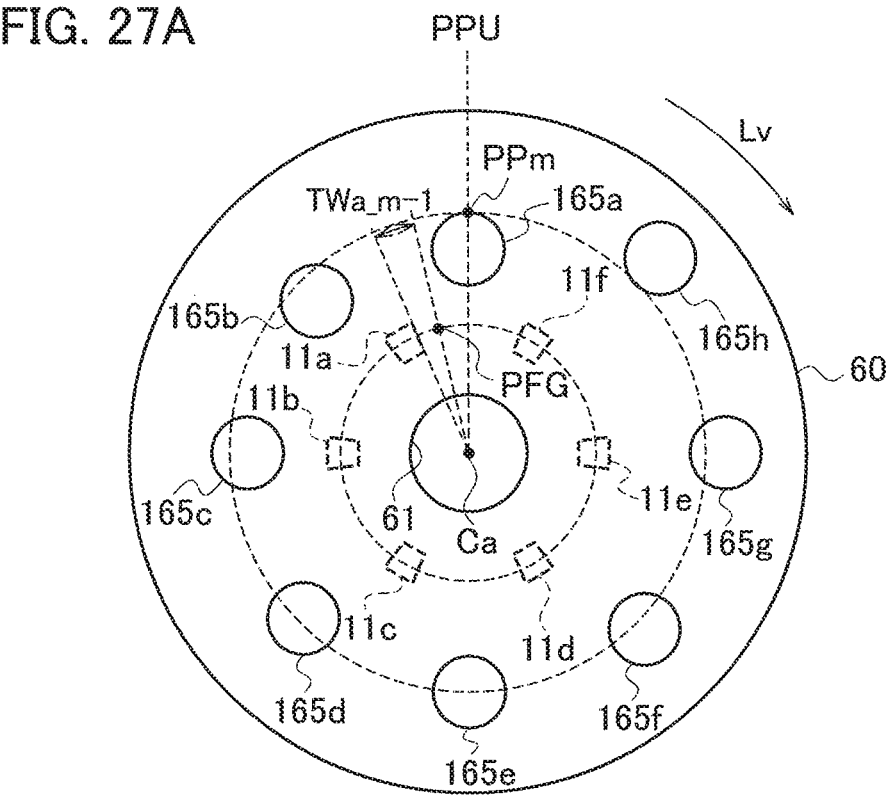
FIGS. 27A and 27B are schematic top views for describing a positional relationship between the respective reaction regions and the detecting position of the optical pickup when the optical pickup moves to a radial position Pm and a positional relationship between the respective FG elements and the detecting position of the turntable rotation detecting sensor.
Figure 27B:
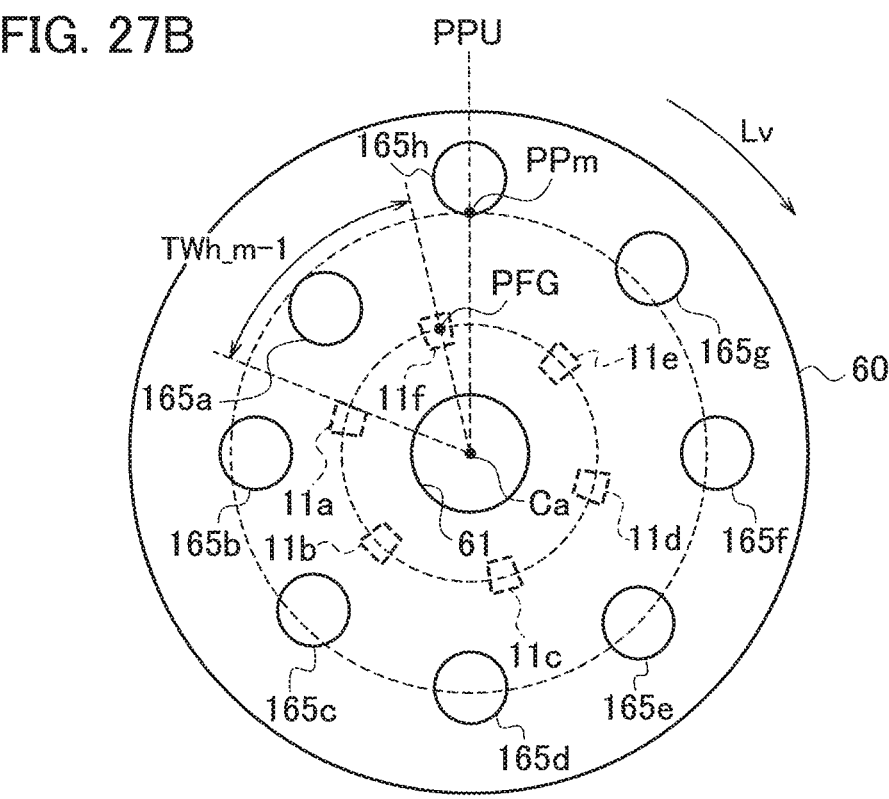

FIG. 27A illustrates a state in which the optical pickup 20 is moved to the radial position PPm and the reaction region 165a is moved to the detecting position PPU. FIG. 27B illustrates a state in which the substrate 60 is rotated from the state shown in FIG. 27A and the reaction region 165h is moved to the detecting position PPU at the radial position PPm. FIG. 27A and FIG. 27B each correspond to FIG. 23.

Figure 28:
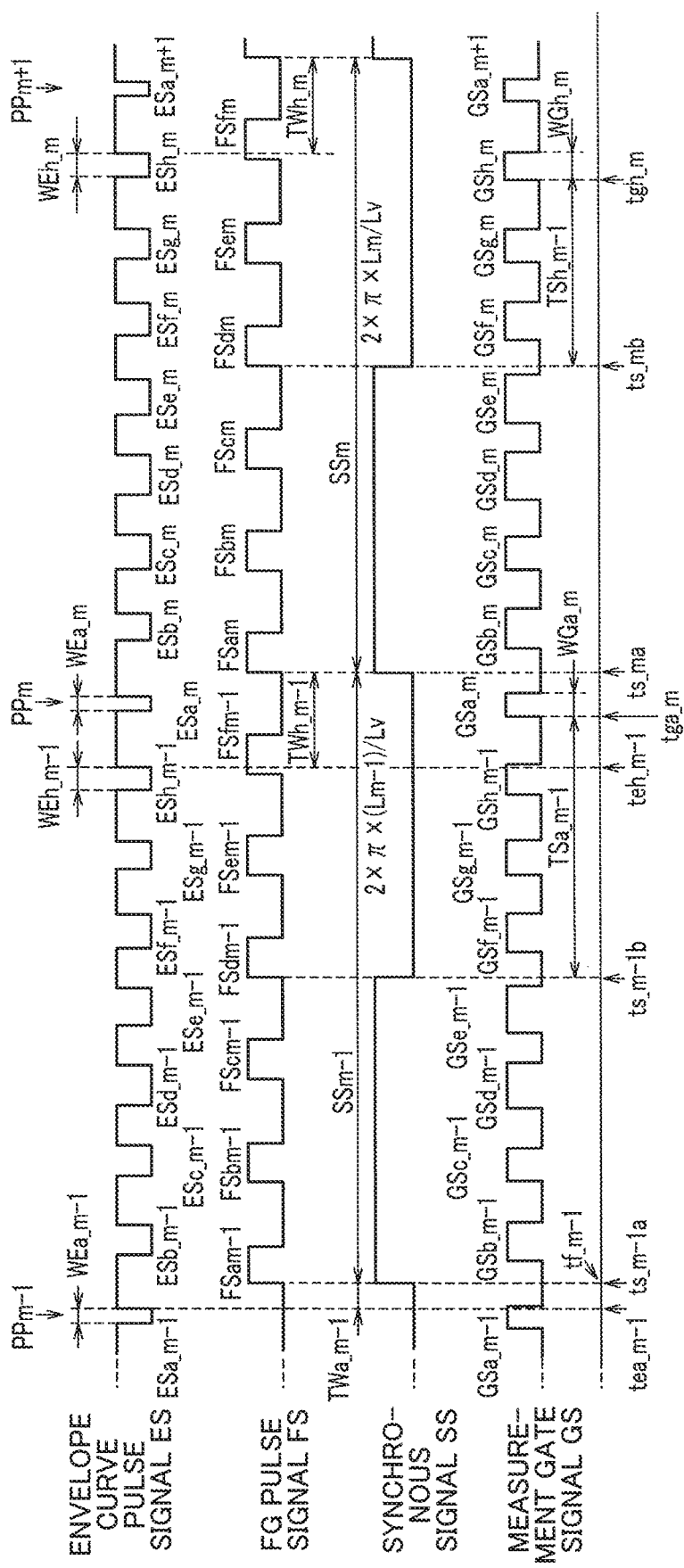
FIG. 28 is a time chart showing a relationship among the envelope curve pulse signal, the FG pulse signal, the synchronous signal, and the measurement gate signal.

FIG. 28 is a time chart showing a relationship among the envelope curve pulse signal ES, the FG pulse signal FS, the synchronous signal SS, and the measurement gate signal GS. FIG. 28 corresponds to FIG. 25.

In step S114, the controller 9 recognizes that the optical pickup 20 is moved to the radial position PPm (n=m) according to the positional information signal PS output from the optical pickup drive circuit 8 (refer to FIG. 6), so as to generate measurement gate signals GSa_m, GSb_m, GSc_m, GSd_m, GSe_m, GSf_m, GSg_m, and GSh_m respectively corresponding to the reaction regions 165a, 165b, 165c, 165d, 165e, 165f, 165g, and 165h. Since all of the reaction regions 165a to 165h are scanned at the radial position PPm, the measurement gate signals GSa_m to GSh_m corresponding to the reaction regions 165a to 165h are thus generated.

As shown in FIG. 28, the measurement gate signals GSa_m to GSg_m (n=m) are generated on the basis of the envelope curve pulse signal ESa_m−1 (n=m−1) in the reaction region 165a before the substrate 60 makes one revolution, as in the case described above.

In particular, the rising point of the measurement gate signal GSa_m (n=m) is set to the time tga_m after a lapse of a time period TSa_m−1 starting from a falling point (time ts_m−1b) of the synchronous signal SSm−1 and calculated according to Equation (2). The rising points of the measurement gate signals GSb_m to GSg_m (n=m) are also set in the same manner.

The measurement gate signal GSh_m (n=m) is generated on the basis of the envelope curve pulse signal ESh_m−1 (n=m−1) in the reaction region 165h before the substrate 60 makes one revolution.

In particular, the rising point of the measurement gate signal GSh_m is set to the time tgh_m after a lapse of a time period TSh_m−1 starting from a falling point (time ts_mb) of the synchronous signal SSm and calculated according to the following Equation (4). The rising points of the following measurement gate signals after the measurement gate signal GSh_m are also set in the same manner.

$$TSh\_m-1 = \frac{\pi \times Lm}{Lv} - \left(\frac{WEh\_m-1}{2} + TWh\_m-1 + \frac{WGh\_m}{2}\right) \quad (4)$$

In Equation (4), Lm (n=m) is a distance from the center Ca of the substrate 60 to the radial position PPm (corresponding to the radial position PPd in FIG. 23), WEh_m−1 is a pulse width of the envelope curve pulse signal ESh_m−1 in the reaction region 165*h* detected by the measurement gate signal GSh_m-1 at the radial position PPm-1, TWh_m-1 is a period from the rising time teh_m-1 of the envelope curve pulse signal ESh_m-1 to the rising time ts_ma of the synchronous signal SSm, and WGh_m is a pulse width of the measurement gate signal GSh_m at the radial position PPm.

The controller 9 thus generates the measurement gate signals GSa_m to GSh_m synchronous with the envelope curve pulse signals ESa_m to ESh_m.

Accordingly, the measurement can be continued such that the reaction region as a target for measurement is shifted depending on the radial position PPm scanned with the laser light 20*a*.

The controller 9 keeps counting the number of pulses of the nanoparticle pulse signal group MS in the respective reaction regions 165*a* to 165*h* after the reaction region 165*a* is shifted to the reaction region 165*e* as a target for measurement, and adds the counted number in each track together.

In step S115, the controller 9 recognizes that the measurement in the respective reaction regions 165*a* to 165*h* is finished according to the positional information signal PS output from the optical pickup drive circuit 8.

In step S116, the controller 9 controls the optical pickup drive circuit 8 to move the optical pickup 20 to the initial position and stop the emission of the laser light 20*a*. The controller 9 controls the turntable drive circuit 4 to stop the rotation of the turntable 10.

In step S117, the controller 9 can normalize the total number of the nanoparticles 82 (pulses) in the respective reaction regions 165*a* to 165*h* by the same method of complementing the total number of the nanoparticles 82 as in a first embodiment.

In accordance with the analysis device 1 and the analysis method according to a second embodiment, the plurality of reaction regions 165 are formed in a spiral in the same direction as the spiral direction of the convex regions 62 and the recesses 63. The determination of the reaction region detected first can sequentially specify the following reaction regions due to a time lag in the detection of the plurality of reaction regions 165.

The analysis device 1 and the analysis method according to a second embodiment thus can specify the respective reaction regions even when the positional information about the reaction regions is not recorded on the substrate so as to analyze biomaterials such as antibodies and antigens.

The analysis device 1 and the analysis method according to a second embodiment generates the measurement gate signal for extracting the nanoparticle pulse signal group from the light reception level signal in each reaction region depending on the detecting position of the optical pickup, in accordance with the turntable rotation detecting signal output from the turntable rotation detecting sensor, the synchronous signal in which the turntable rotation detecting signal is divided into frequencies, and the envelope curve pulse signal generated according to the light reception level signal output from the optical pickup.

Accordingly, the nanoparticle pulse signal group to be detected can be extracted without noise included, so as to improve the accuracy of detecting the nanoparticles 82 to be analyzed.

It should be understood that the present invention is not intended to be limited to the configurations described above, and various modifications will be apparent to those skilled in the art without departing from the scope of the present invention.

For example, although the analysis device 1 according to first and second embodiments detects the rotation of the substrate 60 magnetically by use of the FG elements 11, the rotation of the substrate 60 may be detected optically with an optical sensor, for example.

The analysis device 1 according to first and second embodiments has illustrated the substrate 60 installed on the turntable 10 such that the reaction regions 65 and the reaction regions 165 face down, but is not limited to this configuration. The substrate 60 may be installed such that the reaction regions 65 or the reaction regions 165 face up.

What is claimed is:

1. An analysis device comprising:
   a turntable holding a substrate having a plurality of reaction regions for capturing nanoparticles to be analyzed;
   a turntable drive unit comprising a motor that rotates the turntable;
   a turntable drive circuit that controls the turntable drive unit;
   an optical pickup supported by a guide shaft and driven along the guide shaft in a direction perpendicular to a rotation axis of the turntable, and comprising an objective lens, a emitter that emits laser light through the objective lens to the respective reaction regions, and a receiver that receives reflected light from the respective reaction regions;
   an optical pickup drive circuit that controls an operation of the optical pickup; and
   a processor that controls the turntable drive circuit and the optical pickup drive circuit,
   wherein the plurality of reaction regions are formed at positions different from a center of the substrate,
   the substrate is held by the turntable such that the center is located on the rotation axis of the turntable,
   the optical pickup drive circuit detects a position of the turntable in the direction perpendicular to the rotation axis of the turntable to generate a positional information signal,
   the optical pickup detects a reception level of the reflected light from the respective reaction regions to generate a light reception level signal, and
   the processor controls the turntable drive circuit to rotate the substrate, controls the optical pickup drive circuit to move the optical pickup in the direction perpendicular to the rotation axis of the turntable, and specifies the respective reaction regions in accordance with the positional information signal and the light reception level signal.

2. The analysis device according to claim 1, wherein the substrate is held by the turntable such that the plurality of reaction regions are arranged on a circumference of a common circle of which a center is shifted from the rotation axis of the turntable.

3. The analysis device according to claim 1, wherein the plurality of reaction regions are arranged into a spiral from an inner side to an outer side of the substrate.

4. The analysis device according to claim 1, wherein the processor extracts a nanoparticle pulse signal group from the light reception level signal so as to detect the nanoparticles from the nanoparticle pulse signal group.

5. The analysis device according to claim 4, further comprising:
   a turntable rotation detecting sensor comprising a magnetic sensor that detects a rotation of the turntable to generate a turntable rotation detecting signal; and a frequency dividing circuit that divides the turntable rotation detecting signal into frequencies to generate a synchronous signal synchronous with a rotation period of the substrate, wherein the processor generates an envelope curve pulse signal based on the nanoparticle pulse signal group, and generates a measurement gate signal synchronous with the envelope curve pulse signal according to the envelope curve pulse signal, the turntable rotation detecting signal, and the synchronous signal.

6. The analysis device according to claim 5, wherein the processor extracts the nanoparticle pulse signal group from the light reception level signal by the measurement gate signal in each reaction region depending on a light reception level detecting position of the optical pickup.

7. An analysis method comprising:

rotating a substrate of which a center is a rotation axis, the substrate having a plurality of reaction regions formed at positions different from the center of the substrate to capture nanoparticles to be analyzed;

emitting laser light to the respective reaction regions from a predetermined position in a direction perpendicular to the rotation axis of the substrate and receiving reflected light from the respective reaction regions;

specifying each position of the respective reaction regions in accordance with positional information on the predetermined position and a reception level of the reflected light; and counting the number of pulses generated in the respective reaction regions to measure the number of the nanoparticles captured in the respective reaction regions.

* * * * *